United States Patent [19]
Wasmoen et al.

[11] Patent Number: 5,849,303
[45] Date of Patent: Dec. 15, 1998

[54] RECOMBINANT FELINE IMMUNODEFICIENCY VIRUS SUBUNIT VACCINES EMPLOYING BACULOVIRAL-EXPRESSED ENVELOPE GLYCOPROTEINS DERIVED FROM ISOLATE NCSU-1 AND THEIR USE AGAINST FELINE IMMUNODEFICIENCY VIRUS INFECTION

[75] Inventors: Terri Wasmoen; Hsien-Jue Chu, both of Fort Dodge, Iowa

[73] Assignee: American Home Products Corporation, Madison, N.J.

[21] Appl. No.: 481,700

[22] Filed: Jun. 7, 1995

[51] Int. Cl.$^6$ .......................... A61K 39/12; A61K 39/21; C12N 15/00; C07H 21/04
[52] U.S. Cl. ..................................... 424/199.1; 424/188.1; 424/208.1; 435/172.3; 435/320.1; 536/23.72
[58] Field of Search ............................... 424/188.1, 208.1

[56] References Cited

FOREIGN PATENT DOCUMENTS

| 2 721 031 | 9/1994 | France | C07K 7/08 |
|---|---|---|---|
| WO 92/09632 | 11/1992 | WIPO | C07K 15/04 |
| WO 92/22573 | 12/1992 | WIPO | C07K 7/06 |
| WO 94/02613 | of 1994 | WIPO | 424/188.1 |
| WO 94/06471 | of 1994 | WIPO | 424/188.1 |
| WO 94/16681 | 4/1994 | WIPO | A61K 9/107 |
| WO 95/30019 | 9/1995 | WIPO | C12N 15/86 |

OTHER PUBLICATIONS

FIV Vaccine Studies. II. Coinical Findings, Hematological changes and Kinetics of Blood Lymphocyte Subsets—R. Hofmann–Lehmann, E. Holznagel, A. Aubert, K. Bauer–Pham & H. Lutz—Veterinary Immunopatholgy 46 (1995) 115–125.

FIV Vaccine Studies, I. Immune response to recombinant FIB env Gene Products and Outcome after Challenge infection—H. Lutz, R. Hofmann–Lehmann, K. Bauer–Pham, E. Holznagel, F. Tozzini, M. Bendinelli, G. Ruebel, A. Aubert, D. Davis—Veterinary Immunology & Immunology & Immunopathology 46 (1995) 103–113.

(List continued on next page.)

Primary Examiner—Donald E. Adams
Assistant Examiner—Jeffrey S. Parkin
Attorney, Agent, or Firm—Darby & Darby

[57] ABSTRACT

The present invention pertains to the prevention or lessening of disease in cats caused by Feline Immunodeficiency Virus (FIV). Prevention or lessening of disease is understood to mean the amelioration of any symptoms, including immune system disruptions, that result from FIV infection. The invention provides recombinant proteins produced in a baculovirus expression system having at least one internal gene comprising a DNA sequence that encodes either the entire FIV env region (ENV-ABC), or a DNA sequence consisting of viral nucleotides 6252–8469 of FIV env (ENV-AB), a DNA sequence consisting of viral nucleotides 6252–6722 and 8264–9140 of FIV env (ENV-AC), or immunogenic fragments of any of the foregoing either singly or in combination. By immunogenic fragment is meant any portion of the coding sequence of FIV env polypeptides that induces a beneficial immune response in cats. In another embodiment, the invention encompasses vaccines that comprise one or more of the baculovirus-expressed recombinant FIV proteins described above, with a pharmaceutically acceptable carrier or diluent and a pharmaceutically acceptable adjuvant. In yet another aspect, the invention provides methods for preventing or lessening disease caused by FIV, which is carried out by administering to a feline in need of such treatment the vaccines described above.

6 Claims, 14 Drawing Sheets

OTHER PUBLICATIONS

Expression of Feline Immunodeficiency Virus gag and env Precursor Proteins in Spodoptera Frugiperda Cells and Their Use in Immunodiagnosis—Ernst J. Verschoor, Arno L.W. van Vliet, Herman FD. Egberink, Wim Hesselink, Marian C. Horzinek & Anthony de Ronde—Journal of Clinical Microbiology, Sep., 1993, p. 2350–2355 vol. 31, No. 9.

The Use of Feline Herpesvirus and Baculovirus as Vaccine for the gag and env Genes of Feline Leukaemia Virus, Journal of General Virology (1992) 73, 1811–1818, Richard G. Wardley, et al.

Verschoor et al., 1993, J. Clin. Microbiol. 31:2350–2355.

Talbott et al., 1989, Proc. Natl. Acad. Sci. USA 86:5743–5747.

Starr, R., 1993, Cornell Vet. 83:311–323.

Kidd et al., 1993, Rev. Biotech. 42:137–159.

Haynes, B., 1993, Science 260:1279–1286.

Sparger, E., 1993, "Current thoughts on feline immunodeficiency virus infection" in Feline Infections Diseases, Hoskins et al., eds., W.B. Saunders Co., Philadelphia, pp. 173–191.

Lutz et al., 1995, Vet. Immunol. Immunopath. 46:103–113.

Siebelink et al., 1995, J. Virol. 69:3704–3711.

FIG. 1

```
               10          20          30          40          50          60
                *           *           *           *           *           *
           GGATCCAACA  ATAATTATGG  CAGAAGGATT  TGCAGCCAAT  AGACAATGGA  TAGGACCAGA
           CCTAGGTTGT  TATTAATACC  GTCTTCCTAA  ACGTCGGTTA  TCTGTTACCT  ATCCTGGTCT
               70          80          90         100         110         120
                *           *           *           *           *           *
           AGAAGCTGAA  GAGTTATTAG  ATTTTGATAT  AGCAACACAA  ATGAATGAAG  AAGGGCCACT
           TCTTCGACTT  CTCAATAATC  TAAAACTATA  TCGTTGTGTT  TACTTACTTC  TTCCCGGTGA
              130         140         150         160         170         180
                *           *           *           *           *           *
           AAATCCAGGG  ATGAACCCAT  TTAGGGTACC  TGGAATAACA  GATAAAGAAA  AGCAAGACTA
           TTTAGGTCCC  TACTTGGGTA  AATCCCATGG  ACCTTATTGT  CTATTTCTTT  TCGTTCTGAT
              190         200         210         220         230         240
                *           *           *           *           *           *
           TTGTAACATA  TTACAACCTA  AGTTACAAGA  TTTACGGAAT  GAACTTCAAG  AGGTAAAACT
           AACATTGTAT  AATGTTGGAT  TCAATGTTCT  AAATGCCTTA  CTTGAAGTTC  TCCATTTTGA
              250         260         270         280         290         300
                *           *           *           *           *           *
           AGAAGAAGGA  AATGCAGGTA  AGTTTAGAAG  AACAAGATTT  TTAAGGTATT  CTGATGAACA
           TCTTCTTCCT  TTACGTCCAT  TCAAATCTTC  TTGTTCTAAA  AATTCCATAA  GACTACTTGT
              310         320         330         340         350         360
                *           *           *           *           *           *
           AGTATTGTCC  CCGGTTCATG  CGTTCATAGG  ATATTGTATT  TATTTAGGTA  ATCGAAATAA
           TCATAACAGG  GGCCAAGTAC  GCAAGTATCC  TATAACATAA  ATAAATCCAT  TAGCTTTATT
              370         380         390         400         410         420
                *           *           *           *           *           *
           GTTAGGATCT  TTAAGACATG  ACATTGATAT  TGAAGCACCC  CCCGAAGAGT  GTTATGATAA
           CAATCCTAGA  AATTCTGTAC  TGTAACTATA  ACTTCGTGGG  GGGCTTCTCA  CAATACTATT
              430         440         450         460         470         480
                *           *           *           *       AvrII          *
           TAGAGAGAAG  GGTACAACTG  ACAATATAAA  ATATGGTAGA  CGATGTTGCC  TAGGAACGGT
           ATCTCTCTTC  CCATGTTGAC  TGTTATATTT  TATACCATCT  GCTACAACGG  ATCCTTGCCA
              490         500         510         520         530         540
                *           *           *           *           *           *
           GACTTTGTAC  CTGATTTTAT  TTATAGGATT  AATAATATAT  TCACAGACAG  CCGACGCTCA
           CTGAAACATG  GACTAAAATA  AATATCCTAA  TTATTATATA  AGTGTCTGTC  GGCTGCGAGT
              550         560         570         580         590         600
                *           *           *           *           *           *
           GGTAGTATGG  AGACTTCCAC  CATTAGTAGT  CCCAGTAGAA  GAATCAGAAA  TAATTTTTTG
           CCATCATACC  TCTGAAGGTG  GTAATCATCA  GGGTCATCTT  CTTAGTCTTT  ATTAAAAAAC
              610         620         630         640         650         660
                *           *           *           *           *           *
           GGATTGTTGG  GCACCAGAAG  AACCCGCCTG  TCAGGACTTT  CTTGGGGCAA  TGATACATCT
           CCTAACAACC  CGTGGTCTTC  TTGGGCGGAC  AGTCCTGAAA  GAACCCCGTT  ACTATGTAGA
```

FIG. 3A

```
              670         680         690         700         710         720
               *           *           *           *           *           *
         AAAAGCTAAG  ACAAATATAA  GTATACGAGA  GGGACCTACC  TTGGGGAATT  GGGCTAGAGA
         TTTTCGATTC  TGTTTATATT  CATATGCTCT  CCCTGGATGG  AACCCCTTAA  CCCGATCTCT
              730         740         750         760         770         780
               *           *           *           *           *           *
         AATATGGGCA  ACATTATTCA  AAAAGGCTAC  TAGACAATGT  AGAAGAGGCA  GAATATGGAA
         TTATACCCGT  TGTAATAAGT  TTTTCCGATG  ATCTGTTACA  TCTTCTCCGT  CTTATACCTT
              790         800         810         820         830         840
               *           *           *           *           *           *
         AAGATGGGAT  GAGACTATAA  CAGGACCATC  AGGATGTGCT  AATAACACAT  GTTATAATGT
         TTCTACCCTA  CTCTGATATT  GTCCTGGTAG  TCCTACACGA  TTATTGTGTA  CAATATTACA
              850         860         870         880         890         900
               *           *           *           *           *           *
         TTCAGCAATA  GTACCTGATT  ATCAGCGTTA  TTTAGATAGA  GTAGATACTT  GGTTACAAGG
         AAGTCGTTAT  CATGGACTAA  TAGTCGCAAT  AAATCTATCT  CATCTATGAA  CCAATGTTCC
              910         920         930         940         950         960
               *           *           *           *           *           *
         GAAAATAAAT  ATATCATTAT  GTCTAACAGG  AGGAAAAATG  TTGTACAATA  AAGTTACAAA
         CTTTTATTTA  TATAGTAATA  CAGATTGTCC  TCCTTTTTAC  AACATGTTAT  TTCAATGTTT
              970         980         990        1000        1010        1020
               *           *           *           *           *           *
         ACAATTAAGC  TATTGTACAG  ACCCATTACA  AATCCCACTG  ATCAATTATA  CATTTGGACC
         TGTTAATTCG  ATAACATGTC  TGGGTAATGT  TTAGGGTGAC  TAGTTAATAT  GTAAACCTGG
             1030        1040        1050        1060        1070        1080
               *           *           *           *           *           *
         TAATCAAACA  TGTATGTGGA  ATACTTCACA  AATTCAGGAC  CCTGAAATAC  CACAATGTGG
         ATTAGTTTGT  ACATACACCT  TATGAAGTGT  TTAAGTCCTG  GGACTTTATG  GTGTTACACC
             1090        1100        1110        1120        1130        1140
               *           *           *           *           *           *
         ATGGTGGAAT  CACATGGCCT  ATTATAACAG  TTGTAAATGG  GAAGAGGCAA  AGGTAAAGTT
         TACCACCTTA  GTGTACCGGA  TAATATTGTC  AACATTTACC  CTTCTCCGTT  TCCATTTCAA
             1150        1160        1170        1180        1190        1200
               *           *           *           *           *           *
         TCATTGTCAA  AGAACACAGA  GTCAGCCTGG  GTCATGGCGT  AGAGCAATCT  CGTCATGGAA
         AGTAACAGTT  TCTTGTGTCT  CAGTCGGACC  CAGTACCGCA  TCTCGTTAGA  GCAGTACCTT
             1210        1220        1230        1240        1250        1260
               *           *           *           *           *           *
         ACAAAGAAAT  AGATGGGAGT  GGAGACCAGA  TTTTGAGAGT  GAAAAGGTGA  AAATATCTCT
         TGTTTCTTTA  TCTACCCTCA  CCTCTGGTCT  AAAACTCTCA  CTTTTCCACT  TTTATAGAGA
             1270        1280        1290        1300        1310        1320
               *           *           *           *           *           *
         ACAGTGCAAT  AGCACGAAAA  ACCTAACCTT  TGCAATGAGA  AGTTCAGGAG  ATTATGGAGA
         TGTCACGTTA  TCGTGCTTTT  TGGATTGGAA  ACGTTACTCT  TCAAGTCCTC  TAATACCTCT
```

FIG. 3B

```
       1330       1340       1350       1360       1370       1380
         *          *          *          *          *          *
    AGTAACGGGA GCTTGGATAG AGTTTGGATG TCATAGAAAT AAATCAAACC TTCATACTGA
    TCATTGCCCT CGAACCTATC TCAAACCTAC AGTATCTTTA TTTAGTTTGG AAGTATGACT
       1390       1400       1410       1420       1430       1440
         *          *          *          *          *          *
    AGCAAGGTTT AGAATTAGAT GTAGATGGAA TGTAGGGAGT GATACCTCGC TCATTGATAC
    TCGTTCCAAA TCTTAATCTA CATCTACCTT ACATCCCTCA CTATGGAGCG AGTAACTATG
       1450       1460       1470       1480       1490       1500
         *          *          *          *          *          *
    ATGTGGAAAC ACTCCAAATG TTTCAGGTGC GAATCCTGTA GATTGTACCA TGTATTCAAA
    TACACCTTTG TGAGGTTTAC AAAGTCCACG CTTAGGACAT CTAACATGGT ACATAAGTTT
       1510       1520       1530       1540       1550       1560
         *          *          *          *          *          *
    TAAAATGTAC AAGTTTTCTT TACCAAACGG GTTTACAATG AAGGTAGATG ACCTTATTAT
    ATTTTACATG TTCAAAAGAA ATGGTTTGCC CAAATGTTAC TTCCATCTAC TGGAATAATA
       1570       1580       1590       1600       1610       1620
         *          *          *          *          *          *
    GCATTTCAAT ATGCCAAAAG CTGTAGAAAT GAATAATATT GCTGGAAATT GGTCTTGTAC
    CGTAAAGTTA TACGGTTTTC GACATCTTTA CTTATTATAA CGACCTTTAA CCAGAACATG
       1630       1640       1650       1660       1670       1680
         *          *          *          *          *          *
    ATCTGACTTG CCATCGTCAT GGGGGTATAT GAATTGTAAT TGCCCAAATA GTAGTAGTAG
    TAGACTGAAC GGTAGCAGTA CCCCCATATA CTTAACATTA ACGGGTTTAT CATCATCATC
       1690       1700       1710       1720       1730       1740
         *          *          *          *          *          *
    TTATAGTGGT ACTAAAATGG CATGTCCTAG CAATCGAGGC ATCTTAAGGA ATTGGTATAA
    AATATCACCA TGATTTTACC GTACAGGATC GTTAGCTCCG TAGAATTCCT TAACCATATT
       1750       1760       1770       1780       1790       1800
         *          *          *          *          *          *
    CCCAGTAGCA GGATTACGAC AATCCTTAGA ACAGTATCAA GTTGTAAAAC AACCAGATTA
    GGGTCATCGT CCTAATGCTG TTAGGAATCT TGTCATAGTT CAACATTTTG TTGGTCTAAT
       1810       1820       1830       1840       1850       1860
         *          *          *          *          *          *
    CTTACTGGTC CCAGAGGAAG TCATGGAATA TAAACCTAGA AGGAAAAGGG CAGCTATTCA
    GAATGACCAG GGTCTCCTTC AGTACCTTAT ATTTGGATCT TCCTTTTCCC GTCGATAAGT
       1870       1880       1890       1900       1910       1920
         *          *          *          *          *          *
    TGTTATGTTG GCTCTTGCAA CAGTATTATC TATTGCCGGT GCAGGGACGG GGGCTACTGC
    ACAATACAAC CGAGAACGTT GTCATAATAG ATAACGGCCA CGTCCCTGCC CCCGATGACG
       1930       1940       1950       1960       1970       1980
         *          *          *          *          *          *
    TATAGGGATG GTAACACAAT ACCACCAAGT TCTGGCAACC CATCAAGAAT CTATGGAAAA
    ATATCCCTAC CATTGTGTTA TGGTGGTTCA AGACCGTTGG GTAGTTCTTA GATACCTTTT
```

FIG. 3C

```
              1990        2000        2010        2020        2030       SpeI
                *           *           *           *           *
          GGTGACTGAA  GCCTTAGAGA  TAAACAACTT  AAGGTTAGTT  ACATTAGAGC  ATCAAGTACT
          CCACTGACTT  CGGAATCTCT  ATTTGTTGAA  TTCCAATCAA  TGTAATCTCG  TAGTTCATGA
              2050        2060        2070        2080        2090        2100
                *           *           *           *           *           *
          AGTAATAGGA  TTAAAAGTAG  AAGCTATGGA  AAAATTTTTA  TATACAGCTT  TCGCTATGCA
          TCATTATCCT  AATTTTCATC  TTCGATACCT  TTTTAAAAAT  ATATGTCGAA  AGCGATACGT
              2110        2120        2130        2140        2150        2160
                *           *           *           *           *           *
          AGAATTAGGA  TGTAATCCAA  ATCAATTTTT  CTCCAAAATC  CCTCTTGAGT  TGTGGACAAG
          TCTTAATCCT  ACATTAGGTT  TAGTTAAAAA  GAGGTTTTAG  GGAGAACTCA  ACACCTGTTC
              2170        2180        2190        2200        2210        2220
                *           *           *           *           *           *
          GTATAATATG  ACTATAAATC  AAACAATATG  GAATCATGGA  AATATAACTT  TGGGGGAATG
          CATATTATAC  TGATATTTAG  TTTGTTATAC  CTTAGTACCT  TTATATTGAA  ACCCCCTTAC
              2230        2240        2250        2260        2270        2280
                *           *           *           *           *           *
          GTATAACCAC  ACCAAAGATT  TACAACCAAA  GTTTTATGAA  ATAATAATGG  ACATAGAACC
          CATATTGGTG  TGGTTTCTAA  ATGTTGGTTT  CAAAATACTT  TATTATTACC  TGTATCTTGG
              2290        2300        2310        2320        2330        2340
                *           *           *           *           *           *
          AAATAATGTA  CAAGGGAAAA  CAGGGATACA  ACAATTACCC  AAGTGGGAAG  ATTGGGTAAG
          TTTATTACAT  GTTCCCTTTT  GTCCCTATGT  TGTTAATGGG  TTCACCCTTC  TAACCCATTC
              2350        2360        2370        2380        2390        2400
                *           *           *           *           *           *
          ATGGATAGGA  AATATTCCAC  AATATTTAAA  GGGACTATTG  GGAGGTATCT  TGGGAATAGG
          TACCTATCCT  TTATAAGGTG  TTATAAATTT  CCCTGATAAC  CCTCCATAGA  ACCCTTATCC
              2410        2420        2430        2440        2450        2460
                *           *           *           *           *           *
          ATTAGGAGTG  TTATTATTGA  TTTTATGTTT  ACCTACATTG  GTTGATTGTA  TAAGAAATTG
          TAATCCTCAC  AATAATAACT  AAAATACAAA  TGGATGTAAC  CAACTAACAT  ATTCTTTAAC
              2470        2480        2490        2500        2510        2520
                *           *           *           *           *           *
          TATCCACAAG  ATACTAGGAT  ACACAGTAAT  TGCAATGCCT  GAAGTAGAAG  GAGAAGAAAT
          ATAGGTGTTC  TATGATCCTA  TGTGTCATTA  ACGTTACGGA  CTTCATCTTC  CTCTTCTTTA
              2530        2540        2550        2560        2570        2580
                *           *           *           *           *           *
          ACAACCACAA  ATGGAATTGA  GGAGAAATGG  TAGCCAATTT  GGCATGTCTG  AAAAAGAGGA
          TGTTGGTGTT  TACCTTAACT  CCTCTTTACC  ATCGGTTAAA  CCGTACAGAC  TTTTTCTCCT
              2590        2600        2610        2620        2630        2640
                *           *           *           *           *           *
          GGAATGATGA  AGTATCTCAG  ACTTATTTTA  TAAGGGAGAT  ACTGTGCTAA  GTTCTTCCCT
          CCTTACTACT  TCATAGAGTC  TGAATAAAAT  ATTCCCTCTA  TGACACGATT  CAAGAAGGGA
```

FIG. 3D

```
          2650        2660        2670        2680        2690        2700
            *           *           *           *           *           *
TTGAGGAAGG  TATGTCATAT  GAATCCATTT  CGAACCAAAT  CAAACTAATA  AAGTATGTAT
AACTCCTTCC  ATACAGTATA  CTTAGGTAAA  GCTTGGTTTA  GTTTGATTAT  TTCATACATA
          2710        2720        2730        2740        2750        2760
            *           *           *           *           *           *
TGTAAGGTAA  AAGGAAAAGA  CAAAGAAGAA  GAAGAAAGAA  GAAAGCTTTC  AAGAGGATGA
ACATTCCATT  TTCCTTTTCT  GTTTCTTCTT  CTTCTTTCTT  CTTTCGAAAG  TTCTCCTACT
          2770        2780        2790        2800        2810        2820
            *           *           *           *           *           *
TGACAGAGTT  AGAAGATCGC  TTCAGGAAGC  TATTTGGCAC  GACTTCTACA  ACGGGAGACA
ACTGTCTCAA  TCTTCTAGCG  AAGTCCTTCG  ATAAACCGTG  CTGAAGATGT  TGCCCTCTGT
          2830        2840        2850        2860        2870        2880
            *           *           *           *           *           *
GCACAGTAGA  TTCTGAAGAT  GAACCTCCTA  AAAAAGAAAA  AAGGGTGGAC  TGGGATGAGT
CGTGTCATCT  AAGACTTCTA  CTTGGAGGAT  TTTTTCTTTT  TTCCCACCTG  ACCCTACTCA
          2890        2900        2910        2920        2930        2940
            *           *           *           *           *           *
ATTGGAACCC  TGAAGAAATA  GAAAGAATGC  TTATGGACTA  GGGACTGTTT  ACGAACAAAT
TAACCTTGGG  ACTTCTTTAT  CTTTCTTACG  AATACCTGAT  CCCTGACAAA  TGCTTGTTTA
          2950        2960        2970        2980        2990        3000
            *           *           *           *           *           *
GATAAAAGGA  AATAGCTAAG  CATGACTCAT  AGTTAAAGCG  CTAGCAGCTG  CTTAACCGCA
CTATTTTCCT  TTATCGATTC  GTACTGAGTA  TCAATTTCGC  GATCGTCGAC  GAATTGGCGT
          3010        3020        3030        3040        3050        3060
            *           *           *           *           *           *
AAACCACATC  CTATGTAAAG  CTTGCTAATG  ACGTATAAGT  TGTTCCATTG  TAAGAGTATA
TTTGGTGTAG  GATACATTTC  GAACGATTAC  TGCATATTCA  ACAAGGTAAC  ATTCTCATAT
          3070        3080        3090        3100        3110        3120
            *           *           *           *           *           *
TAACCAGTGC  TTTGTGAAAC  TTCGAGGAGT  CTCTCCGTTG  AGGACTTTCG  AGTTCTCCCT
ATTGGTCACG  AAACACTTTG  AAGCTCCTCA  GAGAGGCAAC  TCCTGAAAGC  TCAAGAGGGA
          3130        3140        3150        3160        3170        3180
            *           *           *           *           *           *
TGAGGCTCCC  ACAGATACAA  TAAATATTTG  AGATTGAACC  CTGTCAAGTA  TCTGTGTAAT
ACTCCGAGGG  TGTCTATGTT  ATTTATAAAC  TCTAACTTGG  GACAGTTCAT  AGACACATTA
          3190        3200        3210        3220
            *           *           *           *
CTTTTTTACC  TGTGAGGTCT  CGGAATCCGG  GCCGAGAACT  TCGCA
GAAAAAATGG  ACACTCCAGA  GCCTTAGGCC  CGGCTCTTGA  AGCGT
```

| CAT ID | PRE-CHALLENGE | | 3 MONTHS POST CHALLENGE | | 8 MONTHS POST CHALLENGE | | 19 MONTHS POST CHALLENGE | |
|---|---|---|---|---|---|---|---|---|
| | VIREMIA† | CD4:CD8 | VIREMIA* | CD4:CD8 | VIREMIA* | CD4:CD8 | VIREMIA∇ | CD4:CD8 |

BAC-AC VACCINATED CATS

| | | | | | | | | |
|---|---|---|---|---|---|---|---|---|
| US2 | NEG | 1.48 | POS | 0.44 | NA | NA | NA | NA |
| 619 | NEG | 2.44 | WK POS | 0.94 | NA | NA | NA | NA |
| 1431 | NEG | 1.79 | POS | 0.91 | NA | NA | NA | NA |
| UE6 | NEG | 2.47 | POS | 1.03 | NA | NA | NA | NA |
| JHP1 | NEG | 1.75 | NEG | 1.25 | NA | NA | NA | NA |

BAC-ENV VACCINATED CATS

| | | | | | | | | |
|---|---|---|---|---|---|---|---|---|
| UX1 | NEG | 2.57 | NEG | 1.23 | POS | 1.18 | POS | 1.38 |
| 1492 | NEG | 1.84 | NEG | 1.50 | NEG | 1.60 | NEG | 1.35 |
| IEZ2 | NEG | 2.61 | NEG | 0.71 | POS | 0.74 | POSΔ | NA |
| X14 | NEG | 2.10 | NEG | 1.18 | NEG | 1.09 | POS | 1.24 |
| X11 | NEG | 1.46 | NEG | 1.36 | NEG | 1.44 | NEG | 1.35 |

CONTROLS

| | | | | | | | | |
|---|---|---|---|---|---|---|---|---|
| 1391 | NEG | 1.44 | POS | 0.69 | POS | 0.75 | POS | 0.83 |
| IEZ5 | NEG | 1.56 | POS | 0.43 | POS | 0.35 | NA | NA |
| IIH2 | NEG | 2.29 | POS | 0.67 | POS | 0.55 | POS | 0.75 |
| 1497 | NEG | 1.53 | NEG | 2.03 | NEG | 1.91 | NEGΔ | NA |
| VN5 | NEG | 1.69 | WK POS | 0.67 | POS | 0.78 | POS | 0.81 |

NA = NOT AVAILABLE
† VIREMIA TESTED BY BOTH PCR AND VIRUS ISOLATION IN CULTURE
* VIREMIA DETECTED BY PCR
∇ VIREMIA DETECTED BY CULTURE ISOLATION
Δ VIREMIA DETECTED AT 18 MONTHS POST CALLENGE (NOT AVAILABLE AT 19 MONTHS POST-CHALLENGE)

FIG. 6

| Time Point After Challenge¥ | Group | % of Cats Viremic | Preventable Fraction¥ | % of Cats CD4:CD8<1.0 | Preventable Fraction¥ |
|---|---|---|---|---|---|
| 3 Months | Controls<br>BAC-ENV | 80%<br>0 | 100% | 80%<br>20% | 75% |
| 8 Months | Controls<br>BAC-ENV | 80%<br>40% | 50% | 80%<br>20% | 75% |
| 19 Months | Controls<br>BAC-ENV | 80%<br>60% | 25% | 80%<br>20% | 75% |

¥ Preventable Fraction = [(% Controls with Sign)−(% Vaccinates with Sign)]÷(% Controls with Sign) × 100

FIG. 7

| CAT ID | PRE-CHALLENGE | | 1.5 MONTHS POST CHALLENGE | | 2.5-3.5 MONTHS POST CHALLENGE Δ | | 22 MONTHS POST CHALLENGE | |
|---|---|---|---|---|---|---|---|---|
| | VIREMIA† | CD4:CD8 | VIREMIA* | CD4:CD8 | VIREMIA* | CD4:CD8 | VIREMIA▽ | CD4:CD8 |

ENV-AB VACCINATES

| | | | | | | | | |
|---|---|---|---|---|---|---|---|---|
| EY1 | NEG | 3.42 | NEG | 2.79 | NEG | 2.96 | DEAD | DEAD |
| FA2 | NEG | 3.91 | POS | 1.58 | POS | 1.04 | POS | 1.54 |
| FC1 | NEG | 1.87 | NEG | 1.21 | NEG | 0.79 | POS | 0.71 |
| FC3 | NEG | 1.70 | NEG | 1.86 | NEG | 1.72 | POS | 1.03 |
| FE2 | NEG | 2.30 | NEG | 1.32 | NEG | 0.74 | NEG | 0.98 |

CONTROLS

| | | | | | | | | |
|---|---|---|---|---|---|---|---|---|
| IT6 | NEG | 3.97 | NEG | 2.05 | NEG | 2.47 | POS | 2.50 |
| JG1 | NEG | 2.08 | POS | 0.65 | POS | 0.65 | NEG | 0.73 |
| JS5 | NEG | 3.22 | NEG | 1.48 | NEG | 0.93 | POS | 1.47 |
| KK2 | NEG | 2.25 | NEG | 1.60 | POS | 0.68 | POS | 0.56 |
| JL1 | NEG | 4.08 | POS | 0.76 | POS | 0.61 | POS | 1.00 |

DEAD = CAT DIED OF CAUSES APPARENTLY NOT RELATED TO FIV INFECTION
Δ  VIREMIA DATA FROM 2.5 MONTHS POST CHALLENGE AND CD4:CD8 DATA FROM 3.5 MONTHS POST-CHALLENGE
†  VIREMIA DETECTED BY PCR AND CULTURE ISOLATION OF VIRUS
*  VIREMIA DETECTED BY PCR DETECTION OF PROVIRUS
▽  VIREMIA DETECTED BY CULTURE ISOLATION OF FIV

FIG. 8

| Time Point After Challenge | Group | % of Cats Viremic | Preventable Fraction¥ | % of Cats CD4:CD8<1.0 | Preventable Fraction¥ |
|---|---|---|---|---|---|
| 1.5 Months | Controls | 40% | | 40% | |
| | BAC-AB | 20% | 50% | 0% | 100% |
| 2.5 to 3.5 Months | Controls | 60% | | 80% | |
| | BAC-AB | 20% | 67% | 40% | 50% |
| 22 Months | Controls | 80% | | 60% | |
| | BAC-AB | 75% | 6% | 50% | 17% |

¥Preventable Fraction = [(% Controls with Sign)−(% Vaccinates with Sign)]÷(% Controls with Sign) × 100

FIG. 9

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Feline immunodeficiency virus
        ( B ) STRAIN: PPR ( v i i i ) POSITION IN GENOME:
        ( B ) MAP POSITION: 6252-6273
        ( C ) UNITS: bp ( x i ) SEQUENCE DESCRIPTION: SEQ ID NO:1:

TCGGATCCAA CAATAATTAT GGCAGAAGG 29

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( v i ) ORIGINAL SOURCE:
        ( A ) ORGANISM: feline immunodeficiency virus
        ( B ) STRAIN: 14

( v i i i ) POSITION IN GENOME:
        ( B ) MAP POSITION: 6723-6745
        ( C ) UNITS: bp ( x i ) SEQUENCE DESCRIPTION: SEQ ID NO:2:

AATCAGGTAC AAAGTCACCG TTC 23

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single (D) TOPOLOGY: linear (i i) MOLECULE TYPE: DNA (genomic)

(v i) ORIGINAL SOURCE:
    (A) ORGANISM: feline immunodeficiency virus
    (B) STRAIN: 14

(v i i i) POSITION IN GENOME:
    (B) MAP POSITION: 6637-6659
    (C) UNITS: bp (x i) SEQUENCE DESCRIPTION: SEQ ID NO:3:

TATAGAAGCA CCCCAAGAAG AG            22

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(i v) ANTI-SENSE: YES (v i) ORIGINAL SOURCE:
        (A) ORGANISM: feline immunodeficiency virus
        (B) STRAIN: 14

(x i) SEQUENCE DESCRIPTION: SEQ ID NO:4:

CATTCCCCCA AAGTTATATT TC            22

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(v i) ORIGINAL SOURCE:
        (A) ORGANISM: feline immunodeficiency virus
        (B) STRAIN: 14

(v i i i) POSITION IN GENOME:
    (B) MAP POSITION: 8264-8285
    (C) UNITS: bp (x i) SEQUENCE DESCRIPTION: SEQ ID NO:5:

TTAGTTACAT TAGAGCATCA AG            22

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: DNA (genomic)

(i v) ANTI-SENSE: YES (v i) ORIGINAL SOURCE:
        (A) ORGANISM: feline immunodeficiency virus
        (B) STRAIN: PPR (v i i i) POSITION IN GENOME:
    (B) MAP POSITION: 9126-9145
    (C) UNITS: bp ( x i ) SEQUENCE DESCRIPTION: SEQ ID NO:6:

TTCTAGATCT TCAGGGTCCC AATACTC 27

( 2 ) INFORMATION FOR SEQ ID NO:7:

( i ) SEQUENCE CHARACTERISTICS:
        ( A ) LENGTH: 3225 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: feline immunodeficiency virus
        ( C ) INDIVIDUAL ISOLATE: NCSU-1

( v i i i ) POSITION IN GENOME:
        ( B ) MAP POSITION: 1-3225
        ( C ) UNITS: bp ( x i ) SEQUENCE DESCRIPTION: SEQ ID NO:7:

GGATCCAACA ATAATTATGG CAGAAGGATT TGCAGCCAAT AGACAATGGA TAGGACCAGA 60

AGAAGCTGAA GAGTTATTAG ATTTTGATAT AGCAACACAA ATGAATGAAG AAGGGCCACT 120

AAATCCAGGG ATGAACCCAT TTAGGGTACC TGGAATAACA GATAAAGAAA AGCAAGACTA 180

TTGTAACATA TTACAACCTA AGTTACAAGA TTTACGGAAT GAACTTCAAG AGGTAAAACT 240

AGAAGAAGGA AATGCAGGTA AGTTTAGAAG AACAAGATTT TTAAGGTATT CTGATGAACA 300

AGTATTGTCC CCGGTTCATG CGTTCATAGG ATATTGTATT TATTTAGGTA ATCGAAATAA 360

GTTAGGATCT TTAAGACATG ACATTGATAT TGAAGCACCC CCCGAAGAGT GTTATGATAA 420

TAGAGAGAAG GGTACAACTG ACAATATAAA ATATGGTAGA CGATGTTGCC TAGGAACGGT 480

GACTTTGTAC CTGATTTTAT TTATAGGATT AATAATATAT TCACAGACAG CCGACGCTCA 540

GGTAGTATGG AGACTTCCAC CATTAGTAGT CCCAGTAGAA GAATCAGAAA TAATTTTTTG 600

GGATTGTTGG GCACCAGAAG AACCCGCCTG TCAGGACTTT CTTGGGCAA TGATACATCT 660

AAAAGCTAAG ACAAATATAA GTATACGAGA GGGACCTACC TTGGGGAATT GGGCTAGAGA 720

AATATGGGCA ACATTATTCA AAAAGGCTAC TAGACAATGT AGAAGAGGCA GAATATGGAA 780

AAGATGGGAT GAGACTATAA CAGGACCATC AGGATGTGCT AATAACACAT GTTATAATGT 840

TTCAGCAATA GTACCTGATT ATCAGCGTTA TTTAGATAGA GTAGATACTT GGTTACAAGG 900

GAAAATAAAT ATATCATTAT GTCTAACAGG AGGAAAAATG TTGTACAATA AAGTTACAAA 960

ACAATTAAGC TATTGTACAG ACCCATTACA AATCCCACTG ATCAATTATA CATTTGGACC 1020

TAATCAAACA TGTATGTGGA ATACTTCACA AATTCAGGAC CCTGAAATAC CACAATGTGG 1080

ATGGTGGAAT CACATGGCCT ATTATAACAG TTGTAAATGG GAAGAGGCAA AGGTAAAGTT 1140

TCATTGTCAA AGAACACAGA GTCAGCCTGG GTCATGGCGT AGAGCAATCT CGTCATGGAA 1200

ACAAAGAAAT AGATGGGAGT GGAGACCAGA TTTTGAGAGT GAAAAGGTGA AAATATCTCT 1260

ACAGTGCAAT AGCACGAAAA ACCTAACCTT TGCAATGAGA AGTTCAGGAG ATTATGGAGA 1320

AGTAACGGGA GCTTGGATAG AGTTTGGATG TCATAGAAAT AAATCAAACC TTCATACTGA 1380

AGCAAGGTTT AGAATTAGAT GTAGATGGAA TGTAGGGAGT GATACCTCGC TCATTGATAC 1440

ATGTGGAAAC ACTCCAAATG TTTCAGGTGC GAATCCTGTA GATTGTACCA TGTATTCAAA 1500

TAAAATGTAC AAGTTTTCTT TACCAAACGG GTTACAATG AAGGTAGATG ACCTTATTAT 1560

GCATTTCAAT ATGCCAAAAG CTGTAGAAAT GAATAATATT GCTGGAAATT GGTCTTGTAC 1620

```
ATCTGACTTG  CCATCGTCAT  GGGGGTATAT  GAATTGTAAT  TGCCCAAATA  GTAGTAGTAG    1680

TTATAGTGGT  ACTAAAATGG  CATGTCCTAG  CAATCGAGGC  ATCTTAAGGA  ATTGGTATAA    1740

CCCAGTAGCA  GGATTACGAC  AATCCTTAGA  ACAGTATCAA  GTTGTAAAAC  AACCAGATTA    1800

CTTACTGGTC  CCAGAGGAAG  TCATGGAATA  TAAACCTAGA  AGGAAAAGGG  CAGCTATTCA    1860

TGTTATGTTG  GCTCTTGCAA  CAGTATTATC  TATTGCCGGT  GCAGGGACGG  GGGCTACTGC    1920

TATAGGGATG  GTAACACAAT  ACCACCAAGT  TCTGGCAACC  CATCAAGAAT  CTATGGAAAA    1980

GGTGACTGAA  GCCTTAGAGA  TAAACAACTT  AAGGTTAGTT  ACATTAGAGC  ATCAAGTACT    2040

AGTAATAGGA  TTAAAAGTAG  AAGCTATGGA  AAAATTTTTA  TATACAGCTT  TCGCTATGCA    2100

AGAATTAGGA  TGTAATCCAA  ATCAATTTTT  CTCCAAAATC  CCTCTTGAGT  TGTGGACAAG    2160

GTATAATATG  ACTATAAATC  AAACAATATG  GAATCATGGA  AATATAACTT  TGGGGGAATG    2220

GTATAACCAC  ACCAAAGATT  TACAACCAAA  GTTTTATGAA  ATAATAATGG  ACATAGAACC    2280

AAATAATGTA  CAAGGGAAAA  CAGGGATACA  ACAATTACCC  AAGTGGGAAG  ATTGGGTAAG    2340

ATGGATAGGA  AATATTCCAC  AATATTTAAA  GGGACTATTG  GGAGGTATCT  TGGGAATAGG    2400

ATTAGGAGTG  TTATTATTGA  TTTTATGTTT  ACCTACATTG  GTTGATTGTA  TAAGAAATTG    2460

TATCCACAAG  ATACTAGGAT  ACACAGTAAT  TGCAATGCCT  GAAGTAGAAG  GAGAAGAAAT    2520

ACAACCACAA  ATGGAATTGA  GGAGAAATGG  TAGCCAATTT  GGCATGTCTG  AAAAAGAGGA    2580

GGAATGATGA  AGTATCTCAG  ACTTATTTTA  TAAGGGAGAT  ACTGTGCTAA  GTTCTTCCCT    2640

TTGAGGAAGG  TATGTCATAT  GAATCCATTT  CGAACCAAAT  CAAACTAATA  AAGTATGTAT    2700

TGTAAGGTAA  AAGGAAAAGA  CAAAGAAGAA  GAAGAAAGAA  GAAAGCTTTC  AAGAGGATGA    2760

TGACAGAGTT  AGAAGATCGC  TTCAGGAAGC  TATTTGGCAC  GACTTCTACA  ACGGGAGACA    2820

GCACAGTAGA  TTCTGAAGAT  GAACCTCCTA  AAAAAGAAAA  AAGGGTGGAC  TGGGATGAGT    2880

ATTGGAACCC  TGAAGAAATA  GAAAGAATGC  TTATGGACTA  GGGACTGTTT  ACGAACAAAT    2940

GATAAAAGGA  AATAGCTAAG  CATGACTCAT  AGTTAAAGCG  CTAGCAGCTG  CTTAACCGCA    3000

AAACCACATC  CTATGTAAAG  CTTGCTAATG  ACGTATAAGT  TGTTCCATTG  TAAGAGTATA    3060

TAACCAGTGC  TTTGTGAAAC  TTCGAGGAGT  CTCTCCGTTG  AGGACTTTCG  AGTTCTCCCT    3120

TGAGGCTCCC  ACAGATACAA  TAAATATTTG  AGATTGAACC  CTGTCAAGTA  TCTGTGTAAT    3180

CTTTTTTACC  TGTGAGGTCT  CGGAATCCGG  GCCGAGAACT  TCGCA                    3225
```

( 2 ) INFORMATION FOR SEQ ID NO:8:

( i ) SEQUENCE CHARACTERISTICS:
        ( A ) LENGTH: 856 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: feline immunodeficiency virus
        ( C ) INDIVIDUAL ISOLATE: NCSU-1

( x i ) SEQUENCE DESCRIPTION: SEQ ID NO:8:

```
Met  Ala  Glu  Gly  Phe  Ala  Ala  Asn  Arg  Gln  Trp  Ile  Gly  Pro  Glu  Glu
 1              5                        10                       15

Ala  Glu  Glu  Leu  Leu  Asp  Phe  Asp  Ile  Ala  Thr  Gln  Met  Asn  Glu  Glu
              20                        25                       30

Gly  Pro  Leu  Asn  Pro  Gly  Met  Asn  Pro  Phe  Arg  Val  Pro  Gly  Ile  Thr
              35                        40                       45
```

```
Asp  Lys  Glu  Lys  Gln  Asp  Tyr  Cys  Asn  Ile  Leu  Gln  Pro  Lys  Leu  Gln
     50                  55                       60

Asp  Leu  Arg  Asn  Glu  Leu  Gln  Glu  Val  Lys  Leu  Glu  Glu  Gly  Asn  Ala
65                       70                  75                            80

Gly  Lys  Phe  Arg  Arg  Thr  Arg  Phe  Leu  Tyr  Ser  Asp  Glu  Gln  Val
               85                       90                       95

Leu  Ser  Pro  Val  His  Ala  Phe  Ile  Gly  Tyr  Cys  Ile  Tyr  Leu  Gly  Asn
               100                 105                      110

Arg  Asn  Lys  Leu  Gly  Ser  Leu  Arg  His  Asp  Ile  Asp  Ile  Glu  Ala  Pro
          115                      120                 125

Pro  Glu  Glu  Cys  Tyr  Asp  Asn  Arg  Glu  Lys  Gly  Thr  Thr  Asp  Asn  Ile
     130                      135                      140

Lys  Tyr  Gly  Arg  Arg  Cys  Cys  Leu  Gly  Thr  Val  Thr  Leu  Tyr  Leu  Ile
145                      150                 155                           160

Leu  Phe  Ile  Gly  Leu  Ile  Ile  Tyr  Ser  Gln  Thr  Ala  Asp  Ala  Gln  Val
               165                      170                      175

Val  Trp  Arg  Leu  Pro  Pro  Leu  Val  Pro  Val  Glu  Glu  Ser  Glu  Ile
               180            185                      190

Ile  Phe  Trp  Asp  Cys  Trp  Ala  Pro  Glu  Glu  Pro  Ala  Cys  Gln  Asp  Phe
          195                 200                      205

Leu  Gly  Ala  Met  Ile  His  Leu  Lys  Ala  Lys  Thr  Asn  Ile  Ser  Ile  Arg
     210                      215                      220

Glu  Gly  Pro  Thr  Leu  Gly  Asn  Trp  Ala  Arg  Glu  Ile  Trp  Ala  Thr  Leu
225                      230                      235                      240

Phe  Lys  Lys  Ala  Thr  Arg  Gln  Cys  Arg  Arg  Gly  Arg  Ile  Trp  Lys  Arg
                    245                      250                      255

Trp  Asp  Glu  Thr  Ile  Thr  Gly  Pro  Ser  Gly  Cys  Ala  Asn  Asn  Thr  Cys
               260                      265                      270

Tyr  Asn  Val  Ser  Ala  Ile  Val  Pro  Asp  Tyr  Gln  Arg  Tyr  Leu  Asp  Arg
          275                      280                 285

Val  Asp  Thr  Trp  Leu  Gln  Gly  Lys  Ile  Asn  Ile  Ser  Leu  Cys  Leu  Thr
     290                      295                 300

Gly  Gly  Lys  Met  Leu  Tyr  Asn  Lys  Val  Thr  Lys  Gln  Leu  Ser  Tyr  Cys
305                      310                      315                      320

Thr  Asp  Pro  Leu  Gln  Ile  Pro  Leu  Ile  Asn  Tyr  Thr  Phe  Gly  Pro  Asn
               325                      330                      335

Gln  Thr  Cys  Met  Trp  Asn  Thr  Ser  Gln  Ile  Gln  Asp  Pro  Glu  Ile  Pro
               340                      345                      350

Gln  Cys  Gly  Trp  Trp  Asn  His  Met  Ala  Tyr  Tyr  Asn  Ser  Cys  Lys  Trp
          355                      360                 365

Glu  Glu  Ala  Lys  Val  Lys  Phe  His  Cys  Gln  Arg  Thr  Gln  Ser  Gln  Pro
     370                      375                 380

Gly  Ser  Trp  Arg  Arg  Ala  Ile  Ser  Ser  Trp  Lys  Gln  Arg  Asn  Arg  Trp
385                      390                 395                           400

Glu  Trp  Arg  Pro  Asp  Phe  Glu  Ser  Glu  Lys  Val  Lys  Ile  Ser  Leu  Gln
               405                      410                      415

Cys  Asn  Ser  Thr  Lys  Asn  Leu  Thr  Phe  Ala  Met  Arg  Ser  Ser  Gly  Asp
               420                 425                      430

Tyr  Gly  Glu  Val  Thr  Gly  Ala  Trp  Ile  Glu  Phe  Gly  Cys  His  Arg  Asn
          435                      440                 445

Lys  Ser  Asn  Leu  His  Thr  Glu  Ala  Arg  Phe  Arg  Ile  Arg  Cys  Arg  Trp
          450                 455                      460

Asn  Val  Gly  Ser  Asp  Thr  Ser  Leu  Ile  Asp  Thr  Cys  Gly  Asn  Thr  Pro
465                      470                      475                      480
```

```
Asn Val Ser Gly Ala Asn Pro Val Asp Cys Thr Met Tyr Ser Asn Lys
            485             490                 495
Met Tyr Lys Phe Ser Leu Pro Asn Gly Phe Thr Met Lys Val Asp Asp
            500             505                 510
Leu Ile Met His Phe Asn Met Pro Lys Ala Val Glu Met Asn Asn Ile
            515             520                 525
Ala Gly Asn Trp Ser Cys Thr Ser Asp Leu Pro Ser Ser Trp Gly Tyr
            530             535                 540
Met Asn Cys Asn Cys Pro Asn Ser Ser Ser Ser Tyr Ser Gly Thr Lys
545                     550                 555                 560
Met Ala Cys Pro Ser Asn Arg Gly Ile Leu Arg Asn Trp Tyr Asn Pro
                565             570                 575
Val Ala Gly Leu Arg Gln Ser Leu Glu Gln Tyr Gln Val Val Lys Gln
                580             585                 590
Pro Asp Tyr Leu Leu Val Pro Glu Glu Val Met Glu Tyr Lys Pro Arg
            595             600                 605
Arg Lys Arg Ala Ala Ile His Val Met Leu Ala Leu Ala Thr Val Leu
    610                 615                 620
Ser Ile Ala Gly Ala Gly Thr Gly Ala Thr Ala Ile Gly Met Val Thr
625                     630                 635                 640
Gln Tyr His Gln Val Leu Ala Thr His Gln Glu Ser Met Glu Lys Val
                645                 650                 655
Thr Glu Ala Leu Glu Ile Asn Asn Leu Arg Leu Val Thr Leu Glu His
                660                 665                 670
Gln Val Leu Val Ile Gly Leu Lys Val Glu Ala Met Glu Lys Phe Leu
            675                 680                 685
Tyr Thr Ala Phe Ala Met Gln Glu Leu Gly Cys Asn Pro Asn Gln Phe
    690                 695                 700
Phe Ser Lys Ile Pro Leu Glu Leu Trp Thr Arg Tyr Asn Met Thr Ile
705                 710                 715                 720
Asn Gln Thr Ile Trp Asn His Gly Asn Ile Thr Leu Gly Glu Trp Tyr
                725                 730                 735
Asn His Thr Lys Asp Leu Gln Pro Lys Phe Tyr Glu Ile Ile Met Asp
            740                 745                 750
Ile Glu Pro Asn Asn Val Gln Gly Lys Thr Gly Ile Gln Gln Leu Pro
        755                 760                 765
Lys Trp Glu Asp Trp Val Arg Trp Ile Gly Asn Ile Pro Gln Tyr Leu
    770                 775                 780
Lys Gly Leu Leu Gly Gly Ile Leu Gly Ile Gly Leu Gly Val Leu Leu
785                 790                 795                 800
Leu Ile Leu Cys Leu Pro Thr Leu Val Asp Cys Ile Arg Asn Cys Ile
                805                 810                 815
His Lys Ile Leu Gly Tyr Thr Val Ile Ala Met Pro Glu Val Glu Gly
            820                 825                 830
Glu Glu Ile Gln Pro Gln Met Glu Leu Arg Arg Asn Gly Ser Gln Phe
            835                 840                 845
Gly Met Ser Glu Lys Glu Glu Glu
    850                 855
```

RECOMBINANT FELINE IMMUNODEFICIENCY VIRUS SUBUNIT VACCINES EMPLOYING BACULOVIRAL-EXPRESSED ENVELOPE GLYCOPROTEINS DERIVED FROM ISOLATE NCSU-1 AND THEIR USE AGAINST FELINE IMMUNODEFICIENCY VIRUS INFECTION

FIELD OF THE INVENTION

The present invention pertains to the treatment and prophylaxis of disease caused by feline immunodeficiency virus (FIV), using baculovirus expressed envelope protein of FIV (env), or immunogenic fragments thereof, as vaccines.

BACKGROUND OF THE INVENTION

Feline immunodeficiency virus (FIV) infection is a significant health problem for domestic cats around the world. As in its human counterpart, infection with FIV causes a progressive disruption in immune function. In the acute phase of infection, the virus causes transient illness associated with symptoms such as lymphadenopathy, pyrexia, and neutropenia. Subsequently, an infected animal enters an asymptomatic phase of 1–2 years before clinical manifestations of immune deficiency become apparent, after which the mean survival time is usually less than one year.

FIV is a typical retrovirus that contains a single-stranded polyadenylated RNA genome, internal structural proteins derived from the gag gene product, and a lipid envelope containing membrane proteins derived from the env gene product (Bendinelli et al., Clin.Microbiol.Rev. 8:87, 1995). The env gene yields a primary translation product of 75–80 kDa (unglycosylated molecular weight); in infected cells, the precursor has an apparent molecular weight of 145–150 kDa due to N-linked glycosylation. The env precursor is cleaved in the Golgi apparatus into the SU and TM proteins (also designated gp95 and gp40, respectively).

Most vaccines against FIV have failed to induce protective immunity. Ineffective vaccines have involved inactivated whole virus, fixed infected cells, recombinant CA and SU proteins, and a synthetic peptide corresponding to the V3 region of SU. In some cases, the vaccine actually enhanced infection after challenge. In one system, vaccination with paraformaldehyde-fixed virus or infected cells resulted in protective immunity (Yamamoto et al., *J. Virol.* 67:601, 1993), but application of this approach by others was unsuccessful (Hosie et al., in *Abstracts of the International Symposium on Feline Retrovirus Research*, 1993, page 50).

Thus, there is a need in the art for an effective vaccine against FIV that utilizes env proteins, or fragments thereof, as immunogens.

SUMMARY OF THE INVENTION

The present invention pertains to the prevention or lessening of disease in cats caused by Feline Immunodeficiency Virus (FIV). Prevention or lessening of disease is understood to mean the amelioration of any symptoms, including immune system disruptions, that result from FIV infection.

The invention provides recombinant proteins produced in a baculovirus expression system having at least one internal gene comprising a DNA sequence that encodes either the entire FIV env region (ENV-ABC), or a DNA sequence consisting of viral nucleotides 6252–8469 of FIV env (ENV-AB), a DNA sequence consisting of viral nucleotides 6252–6722 and 8264–9140 of FIV env (ENV-AC), or immunogenic fragments of any of the foregoing either singly or in combination. By immunogenic fragment is meant any portion of the coding sequence of FIV env polypeptides that induces a beneficial immune response in cats.

In another embodiment, the invention encompasses vaccines that comprise one or more of the baculovirus-expressed recombinant FIV proteins described above, with a pharmaceutically acceptable carrier or diluent and a pharmaceutically acceptable adjuvant.

In yet another aspect, the invention provides methods for preventing or lessening disease caused by FIV, which is carried out by administering to a feline in need of such treatment the vaccines described above.

BRIEF DESCRIPTION OF THE DRAWINGS

FIG. 1 is a graphic illustration of the cloning strategy for the env genes of FIV which involved individually cloning DNA sequences encoding aminoterminal, internal, and carboxyterminal segments of the FIV env gene, followed by stepwise ligation of all three segments to produce an intact env-encoding DNA sequence.

FIG. 3 shows the DNA sequence of the env genes cloned from FIV (NCSU -1 strain) [SEQ. I.D. NO. 7].

FIG. 4 shows the amino acid sequence of the env proteins of FIV as predicted from the DNA sequence of FIG. 3 [SEQ. I.D. NO. 8].

FIG. 6 is a table illustrating the detection of viremia and CD4:CD8 ratios in vaccinated and unvaccinated cats of Experiment 1 after FIV challenge.

FIG. 7 is a table illustrating the preventable fraction for viremia and CD4:CD8 ratio changes in vaccinated and unvaccinated cats following FIV challenge.

FIG. 8 is a table illustrating the detection of viremia and CD4:CD8 ratios in vaccinated and unvaccinated cats of Experiment 2 after FIV challenge.

FIG. 9 is a table illustrating the preventable fraction for viremia and CD4:CD8 changes in vaccinated and unvaccinated cats of Experiment 2 after FIV challenge.

DETAILED DESCRIPTION OF THE INVENTION

Figure 2:
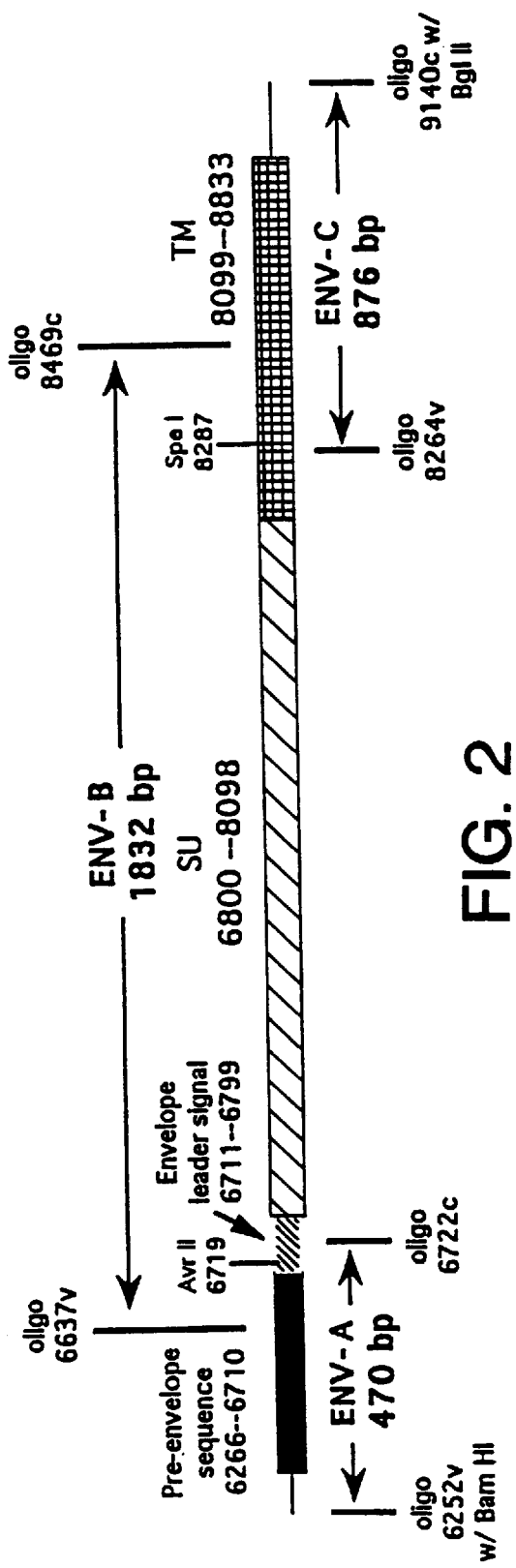
FIG. 2 is a diagrammatic representation of construction comprising the FIV envelope gene detailing the start and endpoints of the ENV-A, ENV-B, and ENV-C fragments in relation to the pre-envelope sequence, the envelope leader signal, the surface (SU) protein, and the transmembrane (TM) protein.
Figure 5:
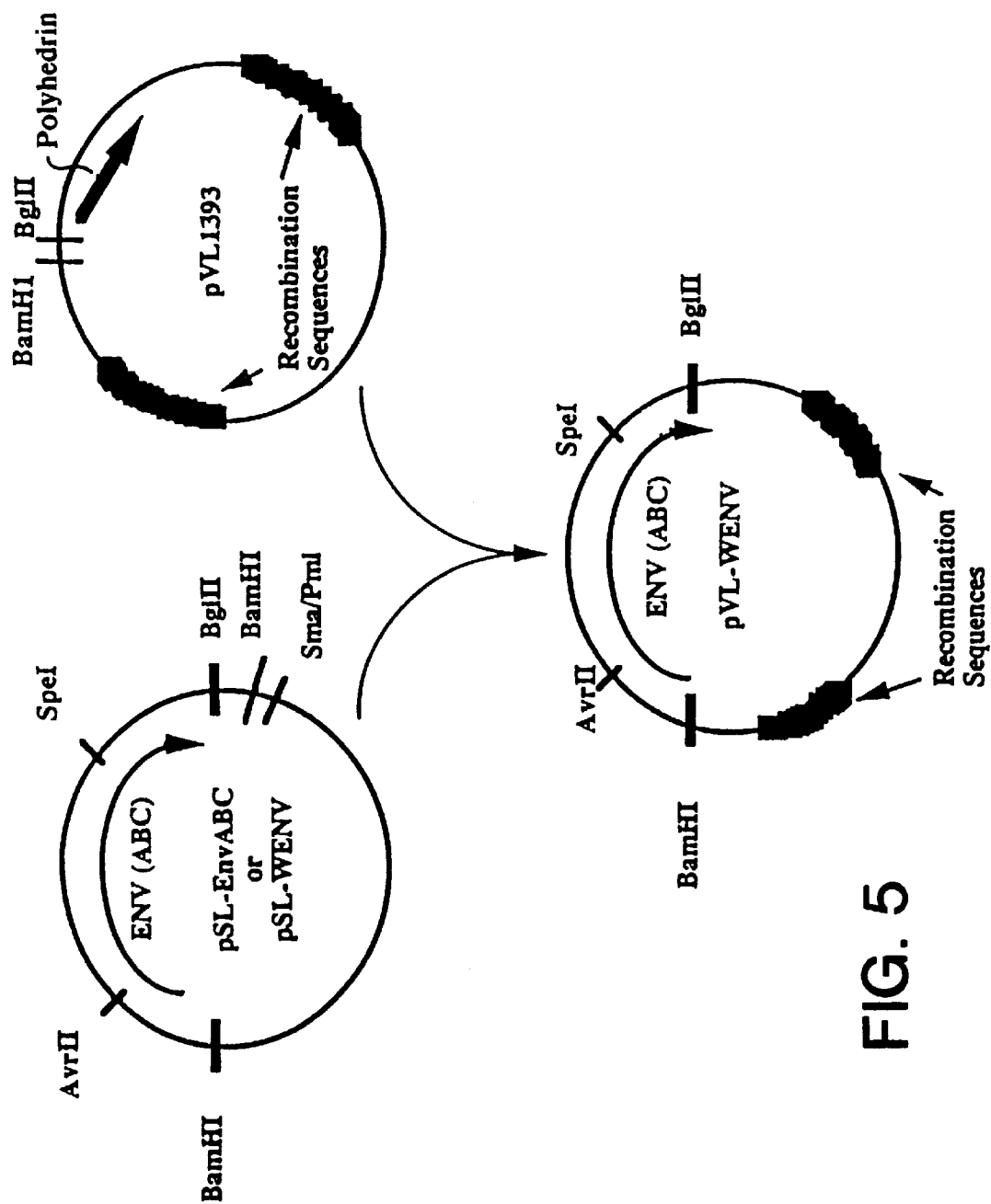
FIG. 5 is a graphic illustration of the subcloning strategy for the FIV env genes into the baculovirus transfer plasmid, pVL-WENV.

All patents, patent applications, and references cited herein are hereby incorporated by reference in their entirety. In the case of inconsistencies, the present disclosure, including definitions, will control.

The vaccine of the present invention may be prepared by creating recombinant baculovirus containing a gene encoding the env proteins of Feline Immunodeficiency Virus (FIV) or immunogenic fragments thereof. Env genes useful in practicing the present invention may be obtained by methods well-known in the art. In one embodiment, viral RNA is reverse-transcribed using endogenous or exogenous reverse transcriptase and the DNA is rendered double-stranded using DNA polymerase. The env-encoding DNA segments are then recovered by restriction enzyme digestion and are amplified by cloning in *E. coli*. In another embodiment, FIV-infected cat cells serve as a source of FIV proviral DNA. In this embodiment, chromosomal DNA is isolated from the cells, and oligonucleotide primers are used to specifically amplify the env genes or fragments therefrom using polymerase chain reaction. This approach is broadly applicable to purifying env genes from different FIV strains or isolates, since primers can be designed from non-polymorphic regions of the FIV genome. The only requirement for FIV env genes for use in the present invention is that the DNA contain sequences that encode env polypeptides, or immunogenic fragments thereof.

FIV env genes isolated by the above methods are first inserted into a transfer plasmid, and the recombinant plasmid is co-transfected with a nuclear polyhedrosis virus linear DNA into appropriate host cells. The DNA from the transfer plasmid is incorporated into the polyhedrosis virus DNA by homologous recombination, and the recombinant viruses are screened for lack of polyhedra and the presence of the desired FIV coding sequence and immunological detection of the desired protein.

DNA encoding the FIV env proteins or fragments therefrom are inserted into a transfer plasmid downstream of a baculovirus promoter. In a preferred embodiment, the polyhedrin protein promoter of baculovirus is used. However, alternate promoter elements which function in insect cells could be used. In the preferred transfer vector, the inserted FIV gene is flanked by DNA sequences which facilitate integration of the plasmid DNA sequences into the polyhedrosis virus DNA by homologous recombination.

In a further embodiment of the present invention, baculovirus can be produced that express less-than-full-length segments of the FIV env proteins. The techniques used to engineer transfer plasmids encoding partial sequences of env are well-known and widely used in the art, as are the methods for production and screening of recombinant baculovirus as detailed in this specification. For example, convenient restriction enzyme recognition sites can be used to obtain fragments of the gene, as described, e.g., Example 1 below. Alternatively, introduction of oligonucleotides containing a stop codon at various points along env DNA will produce a nested set of carboxyterminal-truncated versions of that gene, which can then be incorporated into the transfer vector. Furthermore, sequences that encode different domains on each protein may be recombined, using domains derived from different FIV strains or isolates. It will be apparent to one of ordinary skill in the art that systematic screening of such recombinant baculovirus can establish whether the intact protein, subfragments thereof or multi-strain recombinants thereof, are most preferred in practicing the present invention. Furthermore, as stated above, DNA encoding different fragments of env can be used in a combination vaccine after incorporation into the same, or different, recombinant baculoviruses.

For vaccine preparation, the selected recombinant virus is grown on susceptible cells. Cells are infected with recombinant baculovirus at a multiplicity of infection of 0.05 to 20, preferably 1.0 in 50 ml of media. Cells are separated from supernatant, and the supernatant is then inactivated, and concentrated. Cell material is extracted and cell debris is pelleted. The vaccine is preferably made by combining equal aliquots of both supernatant and cell material. Supernatant and/or cell material or a mixture thereof can be frozen or lyophilized until use.

The amount of supernatant and/or cell material to be used in the vaccine of the present invention is a immunogenically effective amount, generally the amount derived from a culture having a titer of at least $10^4$ $TCID_{50}$/ml and generally no greater than $10^7$ $TCID_{50}$/ml. However, determination of the immunogenically effective amount is within the purview of one of ordinary skill, and is determined, for example by performing a matrix experiment varying the amount of supernatant/cell material and assaying for immunological reaction, as described below.

Supernatant and cell material from insect cell infected with multiple viruses encoding multiple env genes or fragments thereof may be mixed together for vaccination. Furthermore, the virus may be mixed with additional inactivated or attenuated viruses, bacteria, or fungi such as feline leukemia virus, feline panleukopenia virus, feline rhinotracheitis virus, feline calicivirus, feline infectious peritonitis virus, feline *Chlamydia psittaci, Microsporum canis*, or others. In addition, antigens from the above-cited organisms may be incorporated into combination vaccines. These antigens may be purified from natural sources or from recombinant expression systems, or may comprise individual subunits of the antigen or synthetic peptides derived therefrom.

An additional optional component of the present vaccine is a pharmaceutically acceptable adjuvant. Non-limiting examples of suitable adjuvants include squalane and squalene (or other oils of animal origin); block copolymers such as Pluronic® (L121) Saponin; detergents such as Tween®-80; Quil® A, mineral oils such as Drakeol® or Marcol®, vegetable oils such as peanut oil; Corynebacterium-derived adjuvants such as corynebacterium parvum; Propionibacterium-derived adjuvants such as Propionibacterium acne; *Mycobacterium bovis* (Bacillus Calmette and Guerinn, or BCG); interleukins such as interleukin 2 and interleukin-12; monokines such as interleukin 1; tumor necrosis factor; interferons such as gamma interferon; combinations such as saponin-aluminum hydroxide or Quil®-A aluminum hydroxide; liposomes; iscom adjuvant; mycobacterial cell wall extract; synthetic glycopeptides such as muramyl dipeptides or other derivatives; Avridine; Lipid A; dextran sulfate; DEAE-Dextran or DEAE-Dextran with aluminum phosphate; carboxypolymethylene, such as Carbopol®; EMA; acrylic copolymer emulsions such as Neocryle® A640 (e.g. U.S. Pat. No. 5,047,238); vaccinia or animal poxvirus proteins; subviral particle adjuvants such as orbivirus; cholera toxin; dimethyldiocledecylammonium bromide; or mixtures thereof.

In a further embodiment of the present invention, baculovirus cell lysates can be incorporated into liposomes, or encapsulated in peptide-, protein-, or polysaccharide-based microcapsules prior to administration, using means that are known in the art.

At the time of vaccination, the supernatant, cell material or a mixture thereof is thawed (if frozen) or reconstituted (if lyophilized) with a physiologically-acceptable carrier or diluent such as deionized water, saline, phosphate buffered saline, or the like.

The vaccine of the present invention is administered to cats in volumes ranging from 0.5 to 5 milliliters. The vaccine can be administered to cats by subcutaneous, intramuscular, oral, intradermal, or intranasal routes. The number of injections and their temporal spacing may be varied. One to three vaccinations administered at intervals of one to four weeks are usually effective.

The efficacy of the vaccines of the present invention is assessed by the following methods. At about two weeks after the final vaccination, vaccinates and controls are each challenged, preferably through subcutaneous inoculation with 3–20 cat $ID_{50}$ units, preferably 5 cat $ID_{50}$ units of FIV, and preferably the NCSU-1 isolate. Whole blood is obtained from the animals immediately before challenge, and at intervals after challenge, for measurement of a) viremia and b) relative amounts of CD4 and CD8 lymphocytes.

Viremia is measured by isolating mononuclear cells from the blood, and co-culturing the cells with mononuclear cells from uninfected animals. After 7 days of culture, the culture supernatant are tested for FIV by enzyme-linked immunoassay (see Example 4 below).

The ratio of CD4 to CD8 lymphocytes in the circulation of vaccinates and controls is taken as a measure of immune function. Typically, FIV infection causes an inversion of the normal CD4:CD8 ratio of about 1.5–4.0 to a pathological ratio of about 0.5–1.0. The titers of CD4 and CD8 lymphocytes are measured by flow cytometry using specific antibodies (see Example 4 below).

Another measure of immune function is to challenge vaccinates and controls with *Toxoplasma gondii* at 6 months–12 months after the final vaccination. Normally, the severity of *T. gondii*- induced disease symptoms is considerably exacerbated in FIV-infected cats relative to uninfected cats. The severity of the *T. gondii* effect is determined by scoring ocular discharge, nasal discharge, dyspnea, and fever.

It will be understood that amelioration of any of the symptoms of FIV infection is a desirable clinical goal. This includes a lessening of the dosage of medication used to treat FIV-induced symptoms.

The following examples are intended to illustrate the present invention without limitation thereof.

EXAMPLE 1

Generation of Recombinant Baculovirus Expressing FIV ENV Gene

A. Preparation of FIV DNA

FIV-NCSU-1 was isolated from a naturally infected, feline leukemia virus-negative cat and has been described previously (M. B. Tompkins et al. J. Am. Vet. Med. Assoc. 199: 1311–1315, 1991). The virus was passed in a normal specific pathogen-free (SPF) cat (obtained from Liberty Laboratories, Waverly, N.Y.) and FIV-infected peripheral blood mononuclear cells (PBMC) were obtained from whole blood by separation on discontinuous percoll gradients. Briefly, anti-coagulated whole blood was layered over a two step gradient containing 43% Percoll™ (Pharmacia, Piscataway, N.J.) over 62.5% Percoll® diluted in 0.15M NaCl. Gradients were centrifuged at 400×g for 5 minutes followed by 800×g for 20 minutes at 22° C. PBMC were harvested from the gradient interface and washed in phosphate buffered saline containing 5% fetal bovine serum.

FIV was propagated by culture of PBMC's from the FIV-infected cat with PBMC's from normal cats in RPMI 1640 media containing 10% fetal bovine serum, 2.5×10-5 beta-mercaptoethanol, 2 mM L-glutamine, 5 µg/mL concanavalin A, and 20% conditioned media from MLA cells (ATCC TIB 201) as a source of interleukin-2 (IL-2). Cat genomic DNA containing FIV-NCSU-1 proviral sequences was isolated from these cultured cells by lysis of the cells with 0.6% sodium dodecyl sulfate (SDS) in 10 mM Tris-HCl, pH 7.5,. 10 mM EDTA buffer. Chromosomal DNA was precipitated by incubation overnight with 1 mM NaCl followed by centrifugation at 10,000 r.p.m. (Beckman J2, JA-20 rotor) for 40 minutes. The pellet was resuspended in 10 mM Tris-HCl pH 7.5, 10 mM EDTA, 0.1% SDS buffer and digested with ribonuclease A (20 µg/ml) and proteinase K (0.2 mg/ml) at 50° C. for 4 hours. DNA was then purified by sequential extraction with phenol, phenol:chloroform (1:1) and chloroform followed by ethanol precipitation.

B. Cloning of FIV Envelope Sequences

FIV-NCSU-1 envelope DNA sequences were cloned using Polymerase Chain Reaction methods as follows.

1. Envelope Fragment A (ENV-A) Coding strand (6252-V): 5' TCGGATCCAACAATAATTATGGCAGAAGG 3'[SEQ. I.D. NO. 1] Complementary strand (6745-C) 5' AATCAGGTACAAAGTCACCGTTC 3'[SEQ. I.D. NO. 2]

Primer 6252-V corresponds to nucleotides 6252–6273 of FIV strain PPR (GenBank No. M36968) and primer 6745-C (underlined region) corresponds to nucleotides 6723–6745 of FIV strain 14 (GenBank No. 25381). The start codon for envelope protein translation is included in primer 6252-V. Primer 6252-V also has a BamHI restriction enzyme site near the 5' end to facilitate cloning. An AvrII site located at position 6719 also facilitates cloning. Envelope fragment A is 494 bp.

2. Envelope Fragment B (ENV-B) Coding strand (6637-V) 5' TATAGAAGCACCCCAAGAAGAG 3'[SEQ, I.D. NO. 3] Complementary strand (8469-C) 5' CATTCCCCCAAAGTTATATTTC 3'[SEQ. I.D. NO. 4]

Primers 6637-V and 8469-C correspond to nucleotides 6637–6659 and 8448–8469 of FIV 14 strain, respectively. An AvrII site at position 6719 and a SpeI site at position 8288 facilitated cloning. Envelope fragment B is 1833 bp.

3. Envelope Fragment C (ENV-C) Coding strand (8264-V) 5' TTAGTTACATTAGAGCATCAAG 3'[SEQ. I.D. NO. 5] Complementary strand (9145-C) 5' TTCTAGATCTTCAGGGTCCCAATACTC 3'[SEQ. I.D. NO. 6]

Primer 8264-V corresponds to nucleotides 8264–8285 of FIV strain 14 and primer 9145-C (underlined region) corresponds to nucleotides 9126–9145 of FIV strain PPR. Primer 9145-C has a BglII site near the 5' end to facilitate cloning. A SpeI site located at position 8288 also facilitated cloning. Envelope fragment C is 880 bp.

Figure 1:
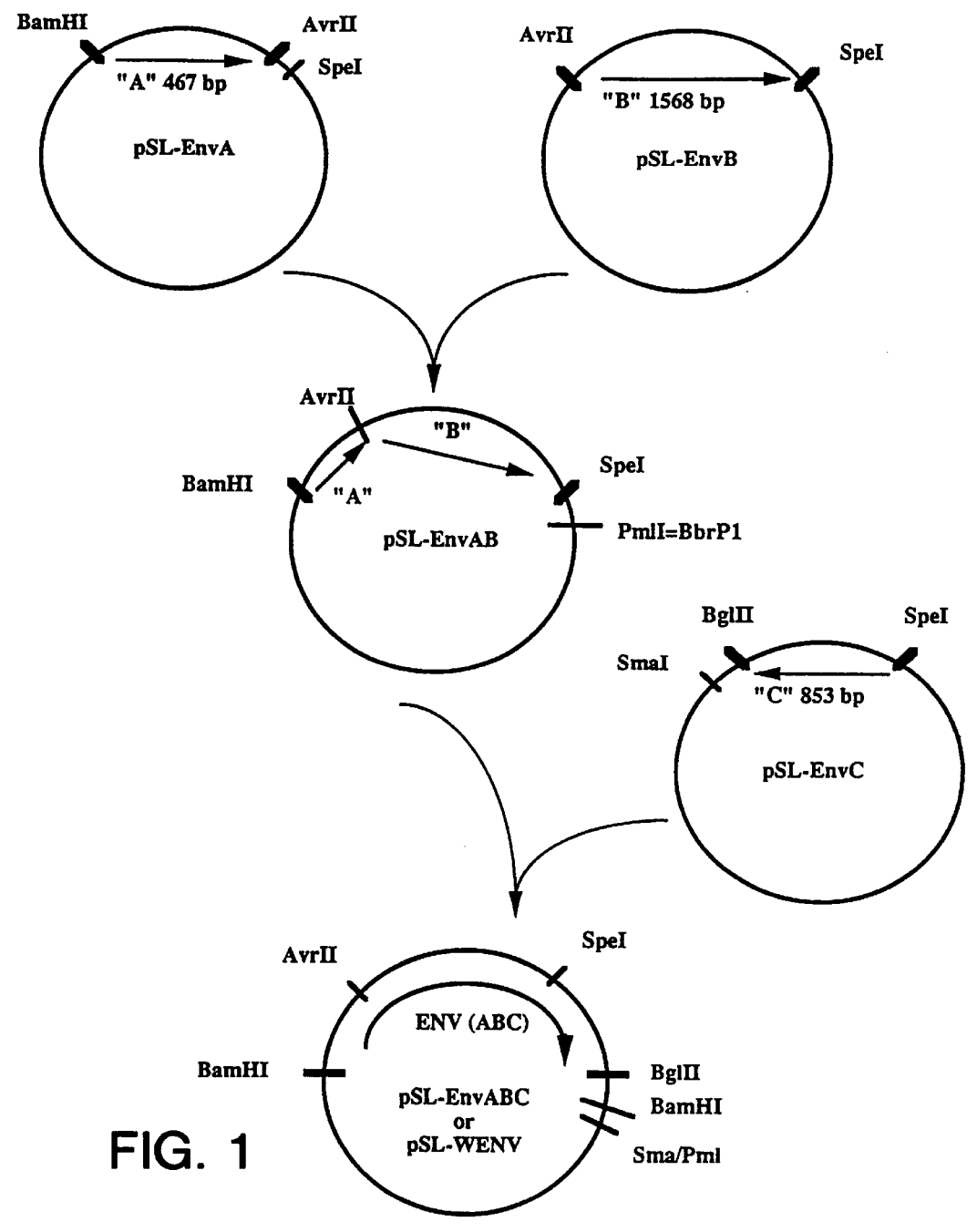

PCR was performed for 35 cycles of 1 min 30 sec at 94° C., 2 min at 56° C., and 2 min at 72° C., followed by one cycle of 8 min at 72° C. Each envelope fragment was isolated by gel electrophoresis and cloned into plasmid pSL1190 using standard methods (Maniatis et al., Molecular Cloning: A Laboratory Manual, 1982, Cold Spring Harbor Press). Envelope A fragment was cut with BamHI and AvrII, envelope B with AvrII and SpeI, and envelope C with SpeI and BglII. Each fragment was then inserted into pSL1190 (FIG. 1). Splicing of the three envelope fragments was done to generate a full length envelope gene. The 1.5 kbp AvrII/SpeI envelope B fragment was-ligated into AvrII/SpeI cut pSL-EnvA to create pSL-EnvAB (FIG. 1). The envAB fragment codes for the entire surface membrane protein (SU) and the first 63 amino acids from the amino-terminus of the transmembrane protein (TM) of FIV-NCSU-1. However, envAB does not contain the membrane spanning domain of TM.

Next, the 0.9 kbp SpeI/SmaI envelope C fragment from pSL-EnvC was ligated into SpeI/BbrPI cut pSL-EnvAB to make pSL-EnvABC or pSL-WEnv (FIG. 1). The WEnv fragment codes for the entire env open reading frame (SU and TM proteins) of FIV NCSU-1 (FIG. 2).

A plasmid containing the "A" region plus the "C" region of the FIV envelope was also created. pSL-ENV-AC was made by ligating the 0.8 kb SPEI/NdeI Env C fragment of pSLENVC into AVRII/NdeI cut pSL-ENV-A (FIG. 1).

Figure 4A:
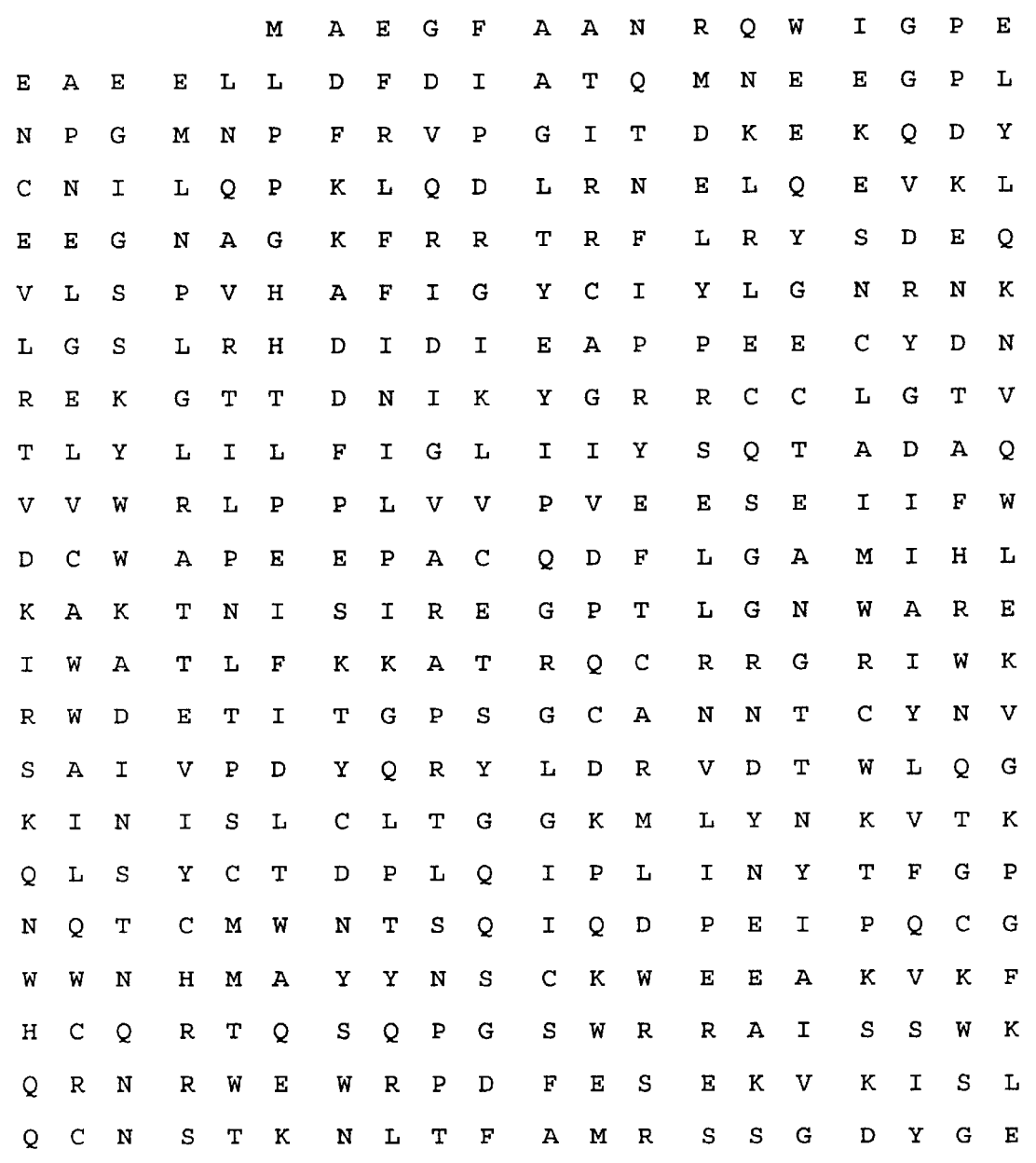
Figure 4B:
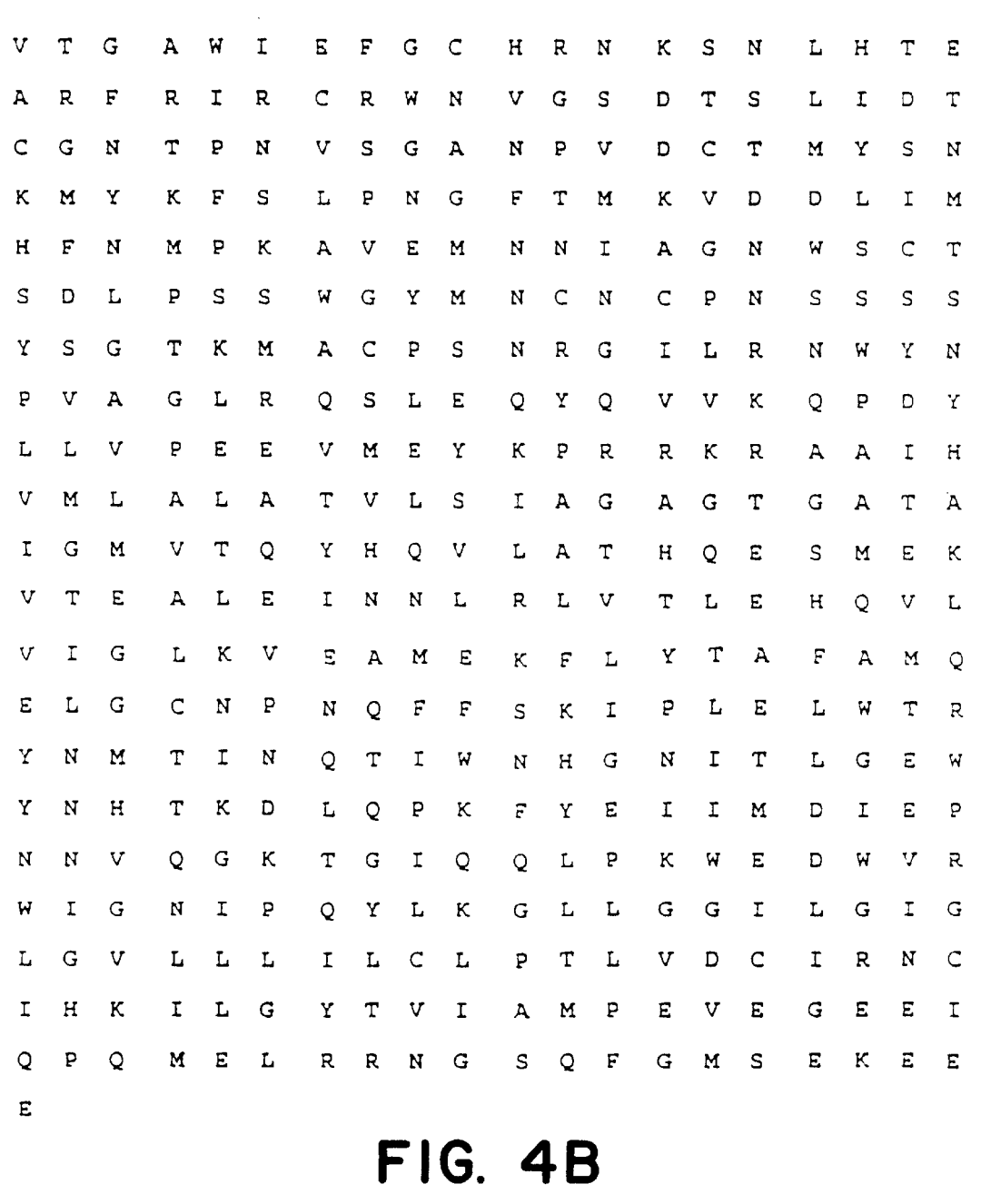

The subcloned genetic elements of FIV-NCSU-1 were sequenced using Sequenase Version 2.0 (United States Biochemical, Cleveland, Ohio)) as described for double-stranded DNA, and the reactions were analyzed using the ABI automated sequencer (Applied Biosystems, Foster City, Calif.). Both DNA strands were sequenced to confirm the results. The DNA sequences were analyzed using the MacVector DNA Analysis software (International Biotechnologies, Inc., New Haven, Conn.). The env DNA sequences were analyzed for open reading frames and compared to the previously published DNA sequences of other FIV isolates. The DNA and predicted amino acid sequences of env and envAB open reading frames of FIV-NCSU-1 are shown in FIGS. 3 and 4.

EXAMPLE 2

Preparation of Baculovirus Expressing FIV-Envelope

The full-length FIV-NCSU-1 gene from the pSL-WENV plasmid was cleaved using BamH1 and BglII and subcloned into the BamH1/BglII cleaved baculovirus transfer plasmid pVL1393 (InVitrogen, San Diego, Calif.) downstream of the polyhedrin promoter (plasmid pVL3-WENV, see FIG. 4). *Spodoptera frugiperda* 9 (Sf9) insect cells were co-transfected with pVL3-WENV plasmid and *Autographa californica* nuclear polyhedrosis virus (AcMNPV) linear DNA according to manufacturer's instructions (InVitrogen, San Diego, Calif.). Recombinant AcMNPV viruses were identified by lack of polyhedra and plaque-purified on Sf9 cells. Virus clone 7.1.4a was selected for preparation of a master seed (BAC-ENV) based on the presence of FIV envelope gene sequences as detected by polymerase chain reaction (using baculovirus primers [forward −44 and reverse +778] and procedure from InVitrogen, San Diego, Calif.) and expression of envelope protein by immunoblot using hyperimmune goat antisera raised against FIV.

A. Preparation of Baculovirus Expressing the AB portion of FIV-Envelope

The AB fragment of the FIV-NCSU-1 envelope gene from the pSL-EnvAB plasmid was cleaved using BamH1 and SpeI and subcloned into the SmaI/BamHI cleaved baculovirus transfer plasmid pVL1393 (InVitrogen, San Diego, Calif.) downstream of the polyhedrin promotor. Transfection and selection of recombinant virus was performed as for BAC-ENV. Virus clone 1.1a was selected for preparation of a master seed (BAC-AB) based on the presence of FIV envelope gene sequences as detected by polymerase chain reaction (using baculovirus primers and procedure from InVitrogen, San Diego, Calif.) and expression of envelope protein by immunoblot using hyperimmune goat antisera raised against FIV.

B. Preparation of Baculovirus Expressing the AC portion of FIV-Envelope

The AC fragment of the FIV-NCSU-1 envelope gene from the pSL-ENV-AC plasmid was cleaved using BamHI and PstI and subcloned into the BamHI/PstI cut baculovirus transfer plasmid pVL1393. Transfection and selection for recombinant virus was performed as for BAC-ENV.

EXAMPLE 3

Production of Vaccines

BAC-ENV virus was grown on *Spodoptera frugiperda* 21 (SF21) cells (InVitrogen, San Diego, Calif.) as follows: Ten 850 cm² roller bottles were seeded with approximately 2×10⁷ SF21 cells in 100 mL of ExCell 401 media (JRH Biosciences, Lenexa, Kans.) and incubated for 18 hours at 27° C. BAC-ENV seed (at 2 passages beyond the master seed virus) was added to the cells at a multiplicity of infection (MOI) of approximately 1.0 in 50 mL of ExCell 401 media and incubated for 1 hour. After this absorption, each roller bottle was adjusted to 200 mL with ExCell 401. After seven days incubation at 27° C., cells and supernatant were harvested and inactivated with 2 mM binary ethylenimine for 3 days at 37° C. Harvested material was centrifuged at 5000×g for 30 minutes in order to remove cell material. The supernatant was concentrated 20-fold through a 10,000 NMW hollow fiber concentrator (Amicon, Beverly, Mass.). The cell fraction was extracted with 100 mL of 0.5% (V/V) Tween-20 (polyoxyethenesorbitan monolaurate), 0.5% (V/V) Triton X100 (polyoxyethylene ether) in phosphate buffered saline for one hour at 22° C. using gentle tumbling, followed by centrifugation at 5000×g for 30 minutes to pellet cell debris. Equal volumes of cell extract and concentrated supernatant were used to blend vaccine.

BAC-AB virus fluids were prepared as described for BAC-ENV.

BAC-AC virus fluids were prepared as described for BAC-ENV.

|  | BAC-ENV Vaccine | BAC-AB Vaccine | BAC-AC Vaccine |
| --- | --- | --- | --- |
| 20X Super | 10.5 mL | 9.5 mL | 10.5 mL |
| 20X Cell Ex. | 10.5 mL | 9.5 mL | 10.5 mL |
| Adjuvant A | 1.5 mL | 1.0 mL | 1.5 mL |
| DEAE Dextran | 7.5 mL | — | 7.5 mL |
| Total Volume | 30 mL | 20 mL | 30 mL |

Adjuvant A is an adjuvant comprising a block copolymer, such as a polyoxypropylene-polyoxyethylene (POP-POE) block copolymer, preferably Pluronic® L121 (e.g. U.S. Pat. No. 4,772,466), and an organic component, such as a metabolizable oil, e.g. an unsaturated turpin hydrocarbon, preferably squalane (2,6,10,15,19,23-hexamethyltetracosane) or squalene. The composition may also include a non-ionic detergent or surfactant, preferably a polyoxyethylene sorbitan monooleate such as a Tween® detergent, most preferably Tween®-80, i.e. polyoxyethylene (20) sorbitan monooleate.

In this adjuvant mixture, the block copolymer, organic oil, and surfactant may be present in amounts ranging from about 10 to about 40 ml/L, about 20 to about 80 ml/L, and about 1.5 to about 6.5 ml/L, respectively. In a preferred embodiment of the stock adjuvant, the organic component is squalane present in an amount of about 40 mL/L, the surfactant is polyoxyethylenesorbitan monooleate (Tween®-80) present in an amount of about 3.2 ml/L, and the POP-POE block copolymer is Pluronic® L121 present in an amount of about 20 ml/L. Pluronic® L121 is a liquid copolymer at 15–40° C., where the polyoxypropylene (POP) component has a molecular weight of 3250 to 4000 and the polyoxyethylene (POE) component comprises about 10–20%, preferably 10%, of the total molecule.

EXAMPLE 4

Vaccine Testing

A. Animals.

Specific-pathogen free (SPF) domestic shorthair cats (Liberty Laboratories, Waverly, N.Y.), both male and female that were greater than 6 months of age were used.

B. Vaccination.

Cats were vaccinated with a 1 mL dose of vaccine administered subcutaneously in the nape of the neck. A second vaccination was administered 21 days later using the same route and dosage. Five cats were vaccinated with each vaccine formulation. Ten cats remained as unvaccinated controls.

C. FIV Challenge.

Fourteen days after the second vaccination cats were challenged with 5 cat $ID_{50}$ of NCSU-1 virus by subcutaneous inoculation. Whole blood was obtained from the cats prior to challenge and periodically after challenge in order to assess virus infection parameters as follows:

1. Detection of Viremia
    a. PCR Detection of FIV proviral DNA

Mononuclear cells were isolated from whole blood using Percoll™ (Pharmacia Biotech, Piscataway N.J.) gradients. $5 \times 10^5$ cells were lysed and 1/10th of the lysate used in a polymerase chain reaction assay with oligonucleotide primers specific to the gag gene of FIV (T L Wasmoen et al. Vet. Immun. Immunopath. 35: 83–93, 1992). FIV amplified DNA was detected by agarose gel electrophoresis and ethidium bromide staining.

b. Tissue Culture Isolation of FIV

Culture isolate of FIV was performed as described previously (Wasmoen et al., Vet. Immuno. Immunopath. 35:83–93, 1992). Mononuclear cells were isolated from whole blood using Percoll™ (Pharmacia Biotech, Piscataway N.J.) gradients. $5 \times 10^5$ cells from FIV-challenged cats were cultured with $1 \times 10^6$ mononuclear cells isolated from uninfected cats. Cultures were fed with RPMI media every 7 days and supernatant tested for the presence of FIV by an enzyme-linked immunosorbent assay (ELISA) that detects FIV p25 antigen (Petcheck ELISA, IDEXX, Portland ME).

2. Lymphocyte Subsets

Leukocytes were isolated from whole blood using Histopaque™ (Sigma Chemical Company, St. Louis Mo.) and lymphocyte subsets quantitated by staining the cells with antibodies specific to CD4 (monoclonal antibody CAT30A), CD8 (monoclonal antibody FLSM 3.357), pan T lymphocytes (monoclonal antibody FLSM 1.572) or B lymphocytes (anti-cat IgG) followed by FACS analysis. These monoclonal antibodies are described elsewhere (M. B. Tompkins et al. Vet. Immunol. Immunopathol. 26:305–317, 1990) and the flow cytometry procedure is the same as previously described (R. V. English et al. J. Infect. Dis. 170:543–552, 1994). CD4:CD8 ratios were calculated.

D. Results.

1. Experiment 1

Two vaccine formulations were tested in this experiment. Vaccine BAC-AC contains baculovirus-expressed envelope sequences from a portion of the N-terminus (outer envelope) and the C-terminus (transmembrane) of the NCSU-1 envelope protein, but lacks a major part of the outer envelope (SU) protein. Vaccine BAC-ENV contains the entire FIV envelope protein encoding sequence as a subunit expressed in baculovirus. Both vaccines were formulated using the same adjuvant. Cats were given two doses of vaccine and challenged with the NCSU-1 strain of FIV. Prior to challenge, all cats had normal CD4:CD8 lymphocyte ratios (i.e., values greater than 1.0) and where negative for FIV virus as detected by tissue culture isolations of virus or PCR detection of proviral DNA (Table 2, FIG. 6). Three months after FIV inoculation, 80% of the control cats were found to be infected with virus and the same cats had CD4:CD8 ratios that were lower than 1.0 (i.e., inverted). Cats vaccinated with BAC-AC showed a similar pattern with 80% infected with FIV virus and 60% showing CD4:CD8 inversions. By comparison, cats vaccinated with BAC-ENV were negative for viremia, however, one cat showed an abnormal CD4:CD8 lymphocyte ratio. Therefore, vaccine ENV-AC showed no prevention of viremia and only 25% prevention of CD4:CD8 inversions. On the other hands, BAC-ENV induced 100% prevention of viremia and 75% prevention of CD4:CD8 inversion (Table 3, FIG. 7). Because of the apparent lack of efficacy for the BAC-AC formulation, the cats in this group were euthanized and not evaluated at later time points in the study.

At eight months after FIV challenge, 80% of the controls, remained viremic and showed CD4:CD8 inversions (Table 2, FIG. 6). By comparison, only two of the BAC-ENV cats were viremic and only one showed a CD4:CD8 inversion (Table 2, FIG. 6). Therefore, the BAC-ENV vaccine showed 50% prevention of viremia, but still showed 70% prevention of CD4:CD8 inversions (Table 3, FIG. 7). At 18 months after FIV challenge, 80% of the controls remained FIV viremic and three of the animals with valid test data still showed CD4:CD8 inversions (Table 2, FIG. 6). By contrast, FIV viremia was detected in three of the BAC-ENV vaccinated cats and four of these cats still had CD4:CD8 ratios in the normal range (Table 2, FIG. 6). Therefore, the vaccine was less effective in preventing viremia at this later time point, however, it was at least 75% effective in preventing the CD4:CD8 ratio inversion associated with FIV infection.

2. Experiment 2

Five cats were vaccinated with a subunit vaccine containing all the outer envelope protein of FIV and a portion of the transmembrane region that was expressed in baculovirus. The response to FIV infection in these vaccinated cats were compared to the response in unvaccinated control cats. Prior to challenge, all cats were aviremic and possessed normal CD4:CD8 lymphocyte ratios (i.e., values greater than 1.0). By 1.5 months after challenge, 40% of control cats were viremic and showed CD4:CD8 lymphocyte ratio inversions (Table 4, FIG. 8). By contrast only one vaccinate was found to be viremic and none showed CD4:CD8 inversions (Table 4, FIG. 8). Therefore, at this early time point, the vaccine was 50% effective in preventing viremia and 100% effective in preventing lymphocyte subclass alterations (Table 5, FIG. 9).

At 2.5 to 3.5 months after FIV challenge, 60% of controls were infected with FIV and 80% had inverted CD4:CD8 ratios (Table 4, FIG. 8). Vaccinates, on the other hand, showed a 20% infection rate and a 40% lymphocyte inversion rate (Table 4, FIG. 8). Therefore, the vaccine was 67% effective in preventing viremia and 50% effective in preventing lymphocyte subset inversions (Table 5, FIG. 9). Cat EY1 in the vaccinated group died at 10 months after challenge of causes apparently unrelated to infection with FIV, because the cat had never shown signs of infection. However, this could not be confirmed by necropsy because of the poor state of the carcass when discovered the day after death. At 22 months after FIV inoculation, 80% of the controls were viremic and 60% had inverted CD4:CD8 lymphocyte ratios (Table 4, FIG. 8). Protection against infection had decreased in the vaccinates as 75% were now viremic and 50% showed 4:CD8 lymphocyte inversions.

In both experiments, the NCSU-1 strain of FIV was used to evaluate vaccine efficacy because this virus has been shown to be virulent in that it causes a persistent infection that leads to an immune deficiency disease in cats (English et al. J. Inf. Dis. 170:543–52, 1994). In the studies presented, persistent viremia and evidence of adverse changes to the immune system (based on inversions of CD4:CD8 lymphocyte ratios below 1.0) were evident in a consistent percentage of control cats. Vaccination with a baculovirus subunit vaccine containing the entire FIV envelope (BAC-ENV) was effective in preventing viremia and CD4:CD8 inversions in a significant portion of cats. Protection against infection was most evident within eight months of FIV challenge and appeared to deteriorate by 19 months. This may indicate that yearly booster vaccination will be necessary to maintain a high level of protective immunity. However, strong protection against CD4:CD8 lymphocyte inversions below 1.0 was evident even at the later time point. Therefore, even in vaccinated cats that were infected with virus, the alterations to the immune system were not as great as found in control cats. The minimum effective dose of antigen was 7 mL of baculovirus-infected whole culture (supernatant and extracted cells).

The vaccine containing the outer envelope protein but lacking the entire transmembrane coding region (BAC-AB) also showed improvement over controls for prevention of viremia and CD4:CD8 lymphocyte inversion at early time points after vaccination. The minimum effective dose of antigen was 9.5 mL of baculovirus-infected whole culture (supernatant and extracted cells) where the antigen was derived from a culture having a titer of at least $10^4$ $TCID_{50}$/ml. On the other hand, the BAC-AC vaccine which lacks the majority of the outer envelope coding region, showed essentially no efficacy in this model.

What is claimed is:

1. A recombinant baculovirus comprising a DNA sequence encoding a feline immunodeficiency virus (FIV) envelope glycoprotein selected from the group consisting of (I) amino acids 1–735 and (ii) amino acids 1–856 of the FIV envelope glycoprotein having the amino acid sequence of SEQ ID NO: 8.

2. A vaccine comprising a recombinant feline immunodeficiency virus (FIV) envelope glycoprotein wherein said protein is produced by insect cells infected with a recombinant baculovirus comprising a DNA sequence encoding an FIV envelope glycoprotein selected from the group consisting of (I) amino acids 1–735 and (ii) amino acids 1–856 of the FIV envelope glycoprotein having the amino acid sequence of SEQ ID NO: 8, a pharmaceutically acceptable carrier or diluent, and a pharmaceutically acceptable adjuvant.

3. The vaccine of claim 2, further comprising an immunogen derived from viruses selected from the group consisting of feline leukemia virus, feline panleucopenia virus, feline rhinotracheitis virus, feline calicivirus, feline infectious peritonitis virus, feline herpesvirus, feline enteric coronavirus, and mixtures thereof.

4. The vaccine of claim 2, further comprising inactivated or attenuated feline *Chlamydia psittaci, Microsporum canis*, or mixtures thereof.

5. A vaccine comprising a first recombinant feline immunodeficiency virus (FIV) envelope glycoprotein, wherein said glycoprotein is produced by insect cells infected with a recombinant baculovirus comprising a DNA sequence encoding amino acids 1–735 of an FIV envelope glycoprotein having the amino acid sequence of SEQ ID NO: 8; a second recombinant FIV envelope glycoprotein, wherein said glycoprotein is produced by insect cells infected with a recombinant baculovirus comprising a DNA sequence encoding amino acids 1–856 of an FIV envelope glycoprotein having the amino acid sequence of SEQ ID NO: 8; a pharmaceutically acceptable carrier or diluent; and a pharmaceutically acceptable adjuvant.

6. A method for preventing or lessening disease caused by feline immunodeficiency virus (FIV) comprising administering to a feline in need of such treatment a vaccine comprising a recombinant FIV envelope glycoprotein wherein said protein is produced by insect cells infected with a recombinant baculovirus comprising a DNA sequence encoding an FIV envelope glycoprotein selected from the group consisting of (I) amino acids 1–735 and (ii) amino acids 1–856 of the FIV envelope glycoprotein having the amino acid sequence of SEQ ID NO: 8, a pharmaceutically acceptable carrier or diluent, and a pharmaceutically acceptable adjuvant.

* * * * *